(12) United States Patent
Levin et al.

(10) Patent No.: US 6,169,068 B1
(45) Date of Patent: Jan. 2, 2001

(54) PULMONARY ADMINISTRATION OF SOLUBLE COMPLEMENT RECEPTOR-1 (SCR1) AND ITS DERIVATIVES

(75) Inventors: James L. Levin, Wellesley, MA (US); Jean F. Regal, Duluth, MN (US); Carol A. Toth, Sharon, MA (US)

(73) Assignees: Avant Immunotherpeutics, Inc., Needham, MA (US); Regents of the University of Minnesota, Minneapolis, MN (US)

( * ) Notice: Under 35 U.S.C. 154(b), the term of this patent shall be extended for 0 days.

(21) Appl. No.: 08/602,761

(22) PCT Filed: Feb. 8, 1994

(86) PCT No.: PCT/US94/01405

§ 371 Date: Aug. 11, 1995

§ 102(e) Date: Aug. 11, 1995

(87) PCT Pub. No.: WO94/17822

PCT Pub. Date: Aug. 18, 1994

Related U.S. Application Data

(63) Continuation-in-part of application No. 08/016,918, filed on Feb. 12, 1993, now abandoned.

(51) Int. Cl.[7] .......................... A61K 38/17; A61K 9/12; A61K 9/14
(52) U.S. Cl. .................. 514/2; 514/8; 424/499
(58) Field of Search .............. 514/2, 8; 530/350; 424/499

(56) References Cited

U.S. PATENT DOCUMENTS

| 5,011,678 | 4/1991 | Wang et al. . |
|---|---|---|
| 5,077,286 | 12/1991 | Bissolino et al. . |
| 5,093,316 | 3/1992 | Lezdey et al. . |
| 5,212,071 | 5/1993 | Fearon et al. . |

FOREIGN PATENT DOCUMENTS

| WO 89/09220 | 10/1989 | (WO) . |
|---|---|---|
| WO 91/05047 | 4/1991 | (WO) . |
| WO 92/16192 | 10/1992 | (WO) . |

OTHER PUBLICATIONS

D.T. Fearon, *Clin. & Exp. Immunol.* 86: 43–46 (1991).

Holme et al., *Blood Reviews* 3:120–129 (1989).

Hubbard et al., *Proc. Natl. Acad. Sci. USA* 86:680–684 (1989).

Mulligan et al., *J. Immunol.* 148:1479–1485 (1992).

Mulligan et al., *J. Clin. Invest.* 90: 1600–1607 (1992).

Regal, Jean F., *Int. Arch. Allergy Appl,. Immunol.* 91:86–94 (1990).

Roosdorp et al., *NTIS Pub.* No. PB91–184259 (Apr. 3, 1990).

Svehag, Sven–Erik, *Complement Inflamm.* 8:359–369 (1991).

Ward et al., *Klin. Wochensehr* 69: 1009–1011 (1991).

Wearley, Lorraine L., *C.R.T.D.C.S.* 8(4):331–394 (1991).

*Primary Examiner*—David L. Fitzgerald
(74) *Attorney, Agent, or Firm*—Leon R. Yankwich; Kenneth P. Zwicker

(57) ABSTRACT

A method is disclosed for treating diseases or disorders involving complement by pulmonary administration of complement inhibitory proteins such as soluble complement receptor type 1 (sCR1). The present invention relates to the direct treatment of certain complement related disorders by administering complement inhibitory proteins via the pulmonary route, in particular, by direct delivery to the lungs by aerosolization of a complement inhibitory protein and subsequent inhalation.

31 Claims, 14 Drawing Sheets

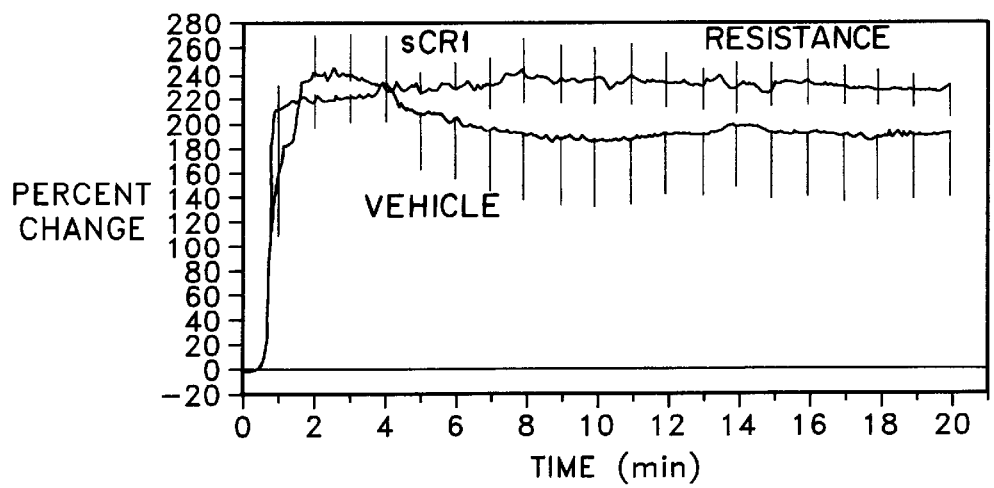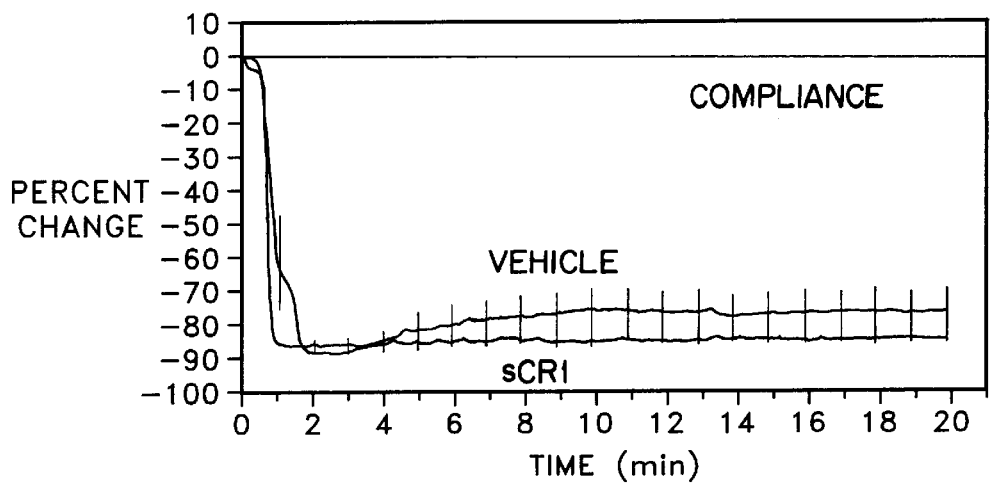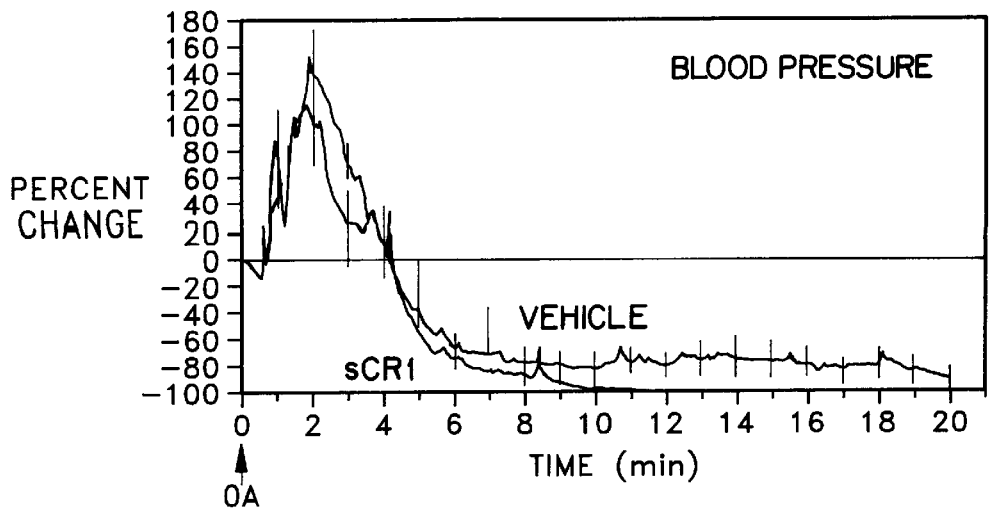

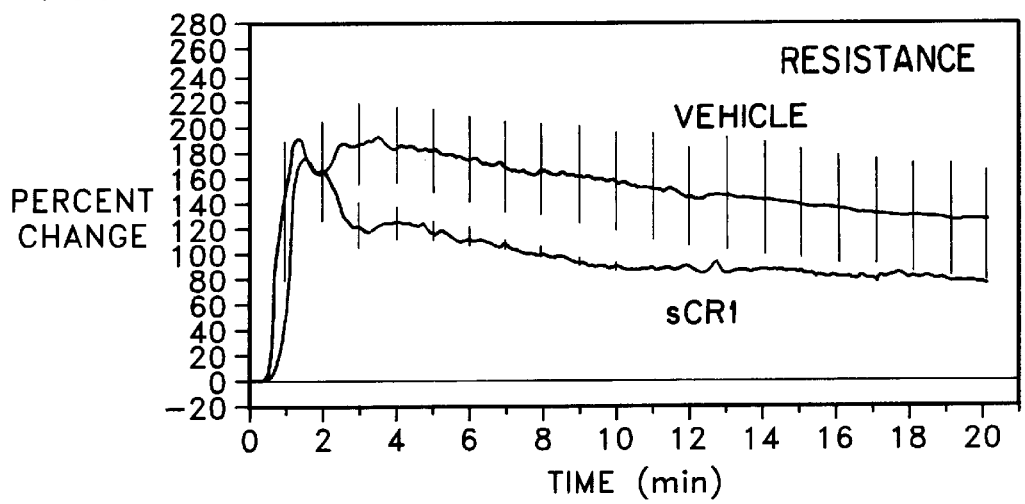
FIG-1D ACTIVELY SENSITIZED
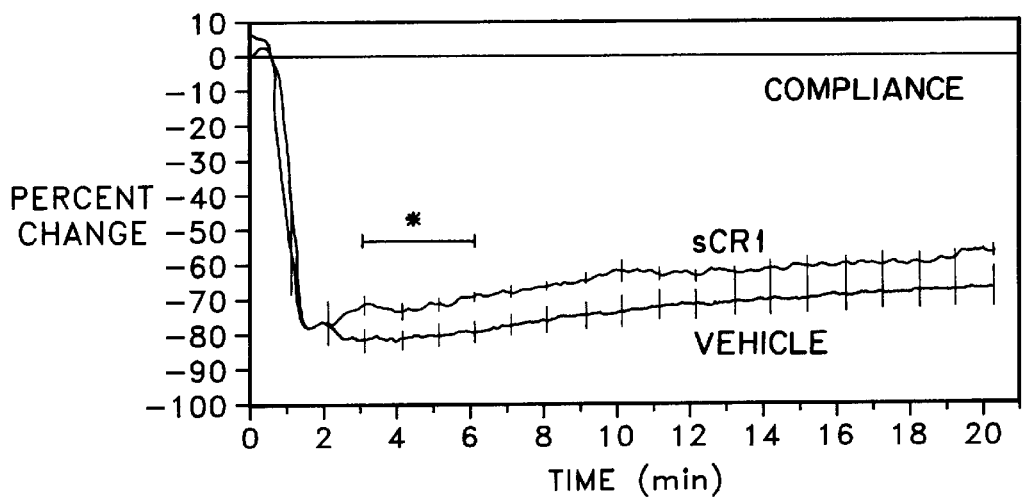
FIG-1E ACTIVELY SENSITIZED
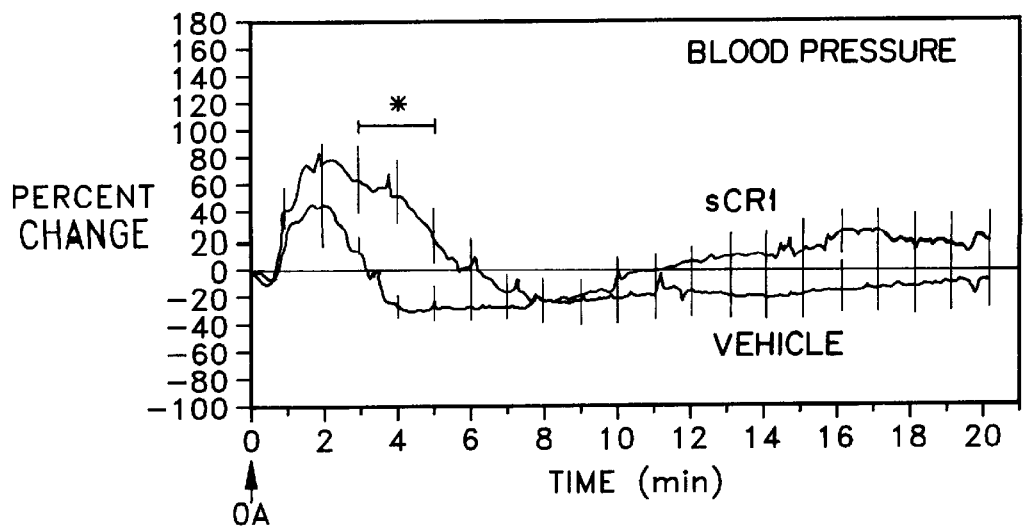
FIG-1F ACTIVELY SENSITIZED FIG-2A PASSIVELY SENSITIZED
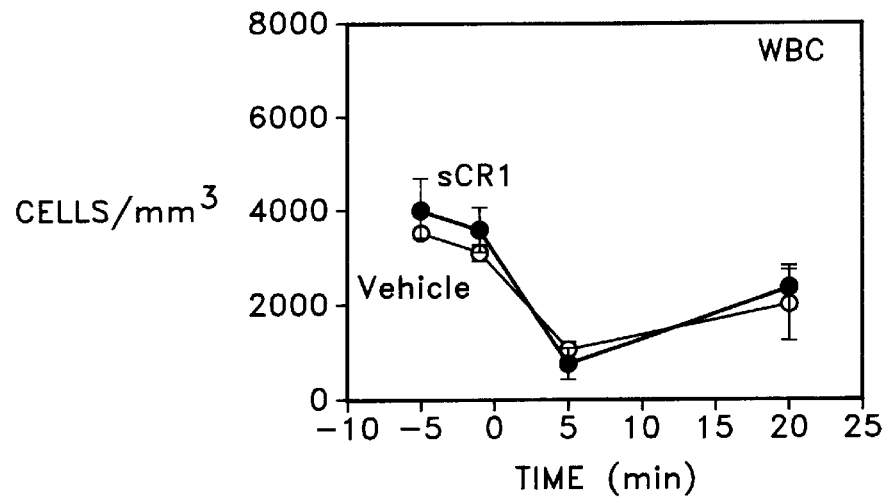
FIG-2B PASSIVELY SENSITIZED
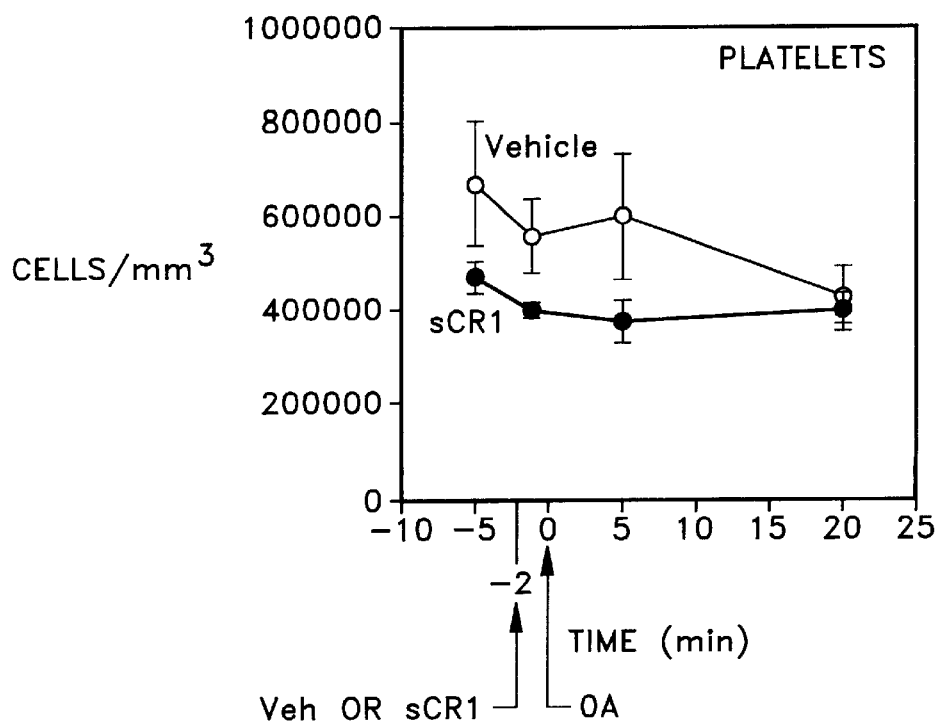

FIG-2C ACTIVELY SENSITIZED
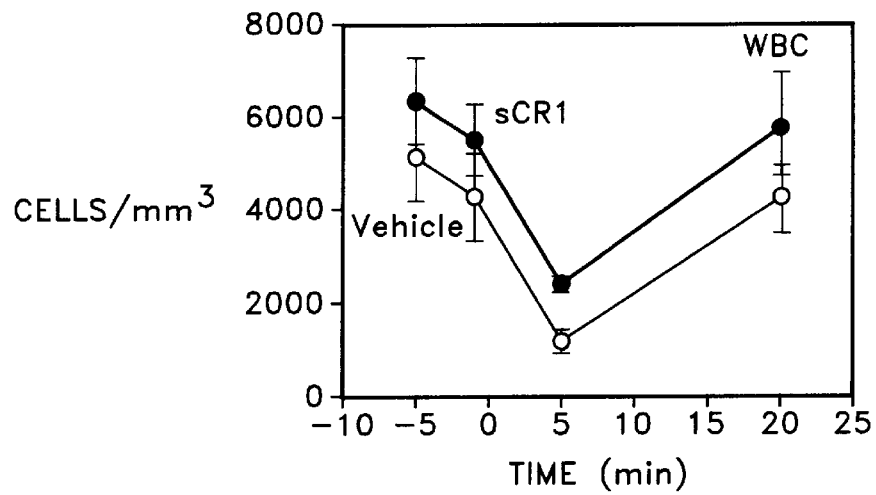
FIG-2D ACTIVELY SENSITIZED
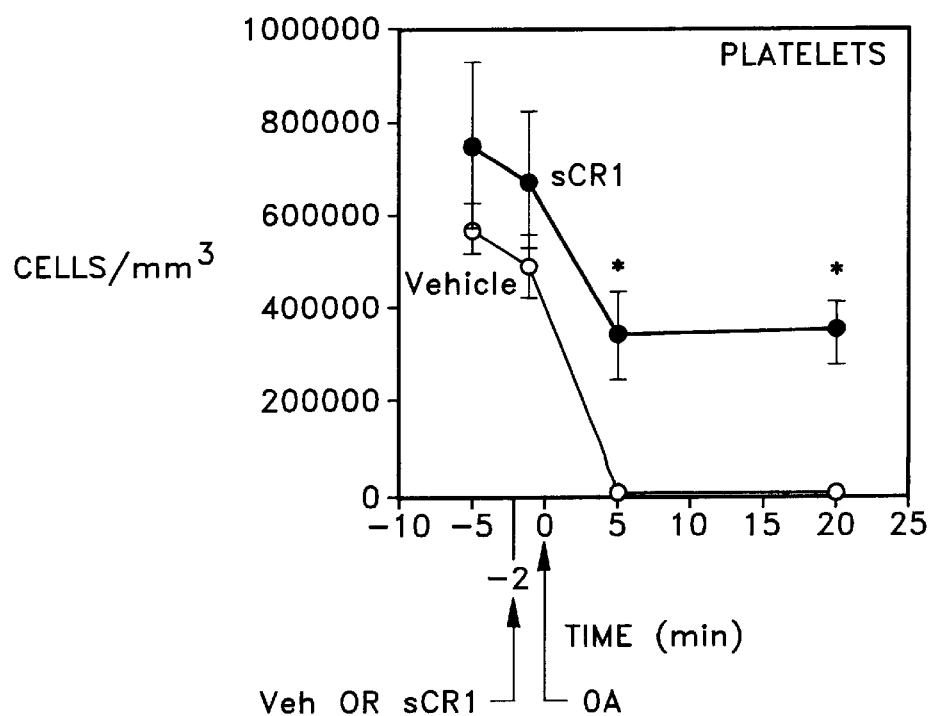

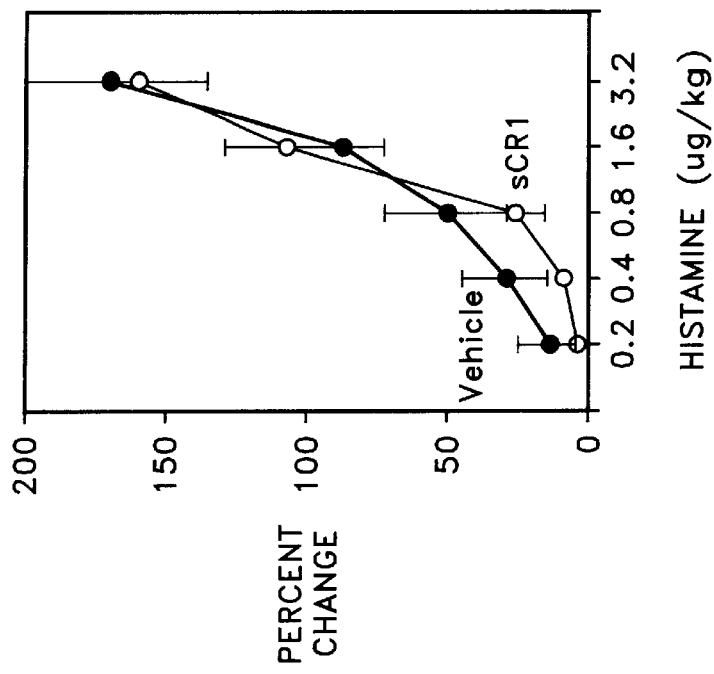
FIG-6B RESISTANCE
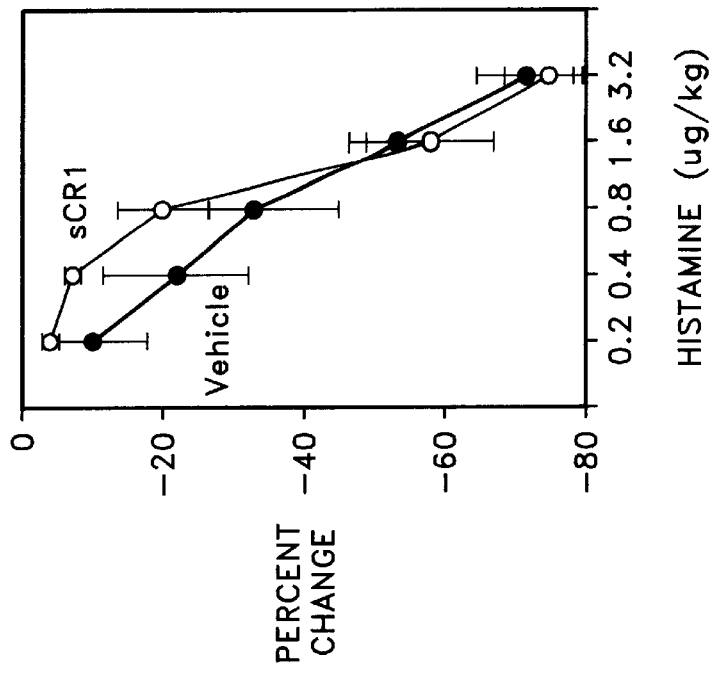
FIG-6A COMPLIANCE

PULMONARY ADMINISTRATION OF SOLUBLE COMPLEMENT RECEPTOR-1 (SCR1) AND ITS DERIVATIVES

This application is a continuation-in-part of U.S. application Ser. No. 08/016,918, filed Feb. 12, 1993 (12.02.93) and now abandoned.

The present invention was made, in part, with funds from NIH grant contract no. S07RR05869, and the Government has certain rights in the invention.

FIELD OF THE INVENTION

The present invention relates to formulations for pulmonary administration by inhalation that comprise a complement inhibitory protein and uses thereof in the prophylactic or therapeutic treatment of disease or disorders involving complement, especially of the lung. In particular, the proteins are complement receptors or fragments thereof or soluble members of the complement receptor family that contain the conserved SCR motif and that are able to inhibit complement activity. More particularly the present invention relates to the direct treatment of certain complement related lung disorders by administering complement receptor proteins via the pulmonary route, in particular, direct delivery to the lungs of a complement receptor protein by aerosolization and subsequent inhalation. The invention also relates to use of a complement inhibitory protein to treat bronchoconstriction or anaphylaxis, or both.

BACKGROUND OF THE INVENTION

The Complement System

The complement system is a group of proteins that constitute about 10 percent of the globulins in the normal serum of humans (Hood, L. E., et al., 1984, Immunology, 2d Ed., The Benjamin/Cummings Publishing Co., Menlo Park, Calif., p. 339). Complement (C) plays an important role in the mediation of immune and allergic reactions (Rapp, J. J. and Borsos, T, 1970, Molecular Basis of Complement Action, Appleton-Century-Crofts (Meredity), New York). The activation of complement components leads to the generation of a group of factors, including chemotactic peptides that mediate the inflammation associated with complement dependent diseases. The sequential activation of the complement cascade may occur via the classical pathway involving antigen-antibody complexes, or by an alternative pathway which involves the recognition of certain cell wall polysaccharides. The activities mediated by activated complement proteins include lysis of target cells, chemotaxis, opsonization, stimulation of vascular and other smooth muscle cells, and functional aberrations such as degranulation of mast cells, increased permeability of small blood vessels, directed migration of leukocytes, and activation of B lymphocytes and macrophages (Eisen, H. N., 1974, Immunology, Harper & Row Publishers, Inc. Hagerstown, Md., p. 512).

During proteolytic cascade steps, biologically active peptide fragments, the anaphylatoxins C3a, C4a, and C5a (See WHO Scientific Group, 1977, WHO Tech, Rep. Ser. 606:5 and references cited therein), are released from the third (C3), fourth (C4), and fifth (C5) native complement components (Hugli, T. E., 1981, CRC Crit. Rev. Immunol. 1:321; Bult, H. and Herman, A. G., 1983, Agents Actions 13:405).

Complement Receptors

COMPLEMENT RECEPTOR 1 (CR1). The human C3b/C4b receptor, termed CR1 or CD35, is present on erythrocytes, monocytes/macrophages, granulocytes, B cells, some T. cells, splenic follicular dendritic cells, and glomerular podocytes (Fearon D. T., 1980, J. Exp. Med. 152:20, Wilson, J. G., et al., 1983, J. Immunol. 131:684; Reynes, M., et al., 1976 N. Engl. J. Med. 295:10; Kazatchkine, M. D., et al., 1982, Clin. Immunol. Immunopathol. 27:210). CR1 specifically binds C3b, C4b and iC3b.

CR1 can inhibit the classical and alternative pathway C3/C5 convertases and act as a cofactor for the cleavage of C3b and C4b by factor I, indicating that CR1 also has complement regulatory functions in addition to serving as a receptor (Fearon, D. T., 1979, Proc. Natl. Acad. Sci. U.S.A. 76:5867; Iida, K. I. and Nussenzweig, V., 1981, J. Exp. Med. 153:1138). In the alternative pathway of complement activation, the bimolecular complex C3b,Bb is a C3 enzyme (convertase). CR1 (and factor H, at higher concentrations) can bind to C3b and can also promote the dissociation of C3b,Bb. Furthermore, formation of C3b,CR1 and (C3b,H) renders C3b susceptible to irreversible proteolytic inactivation by factor I, resulting in the formation of inactivated C3b (iC3b). In the classical pathway of complement activation, the complex C4b,2a is the C3 convertase.

CR1 (and C4 binding protein, C4bp, at higher concentrations) can bind to C4b, and can also promote the dissociation of C4b,2a. The binding renders C4b susceptible to irreversible proteolytic inactivation by factor I through cleavage to C4c and C4d (inactivated complement proteins).

CR1 has been shown to have homology to complement receptor type 2 (CR2) (Weis, J. J., et al., 1986, Proc. Natl. Acad. Sci. U.S.A. 83:5639–4643). CR1 is a glycoprotein comprising multiple short consensus repeats (SCRs) arranged in 4 long homologous repeats (LHRs). The most C-terminal LHR called LHR-D is followed by 2 additional SCRs, a transmembrane region and a cytoplasmic region (Klickstein, et al., 1987, J. Exp. Med., 165:1095; Klickstein, et al., 1988, J. Exp. Med., 168:1699–1717). Erythrocyte CR1 appears to be involved in the removal of circulating immune complexes in autoimmune patients and its levels may correlate with the development of AIDS (Inada, et al., 1986, AIDS Res. 2:235; Inada, et al., 1989, Ann. Rheu. Dis. 4:287).

Four allotypic forms of CR1 have been found, differing by increments of 40,000–50,000 daltons molecular weight. The two most common forms, the F and S allotypes, also termed the A and B allotypes, have molecular weights of 250,000 and 290,000 daltons (Dykman, T. R., et al., 1983, Proc. Natl. Acad. Sci. U.S.A. 80:1698; Wong, W. W., et al., 1983, J. Clin. Invest. 72:685), respectively, and two rarer forms have molecular weights of 210,000 and 290,000 daltons (Dykman, T. R., et al., 1984, J. Exp. Med. 159:6891; Dykman, T. R., et al., 1985, J. Immunol. 134:1787). These differences apparently represent variations in the polypeptide chain of CR1, rather than glycosylation state, because they were not abolished by treatment of purified receptor protein with endoglycosidase F (Wong, W. W., et al., 1983, J. Clin. Invest. 72:685), and they were observed when receptor allotypes were biosynthesized in the presence of the glycosylation inhibitor tunicamycin (Lublin, D. M., et al., 1986, J. Biol. Chem. 261:5736). All four CR1 allotypes have C3b-binding activity (Dykman, T. R., et al., 1983, Proc. Natl. Acad. Sci. U.S.A. 80:1698; Wong, W. W., et al., 1983, J. Clin. Invest. 72:685; Dykman, T. R., et al., 1984, J. Exp. Med., 159:691; Dykman, T. R., et al., 1985, J. Immunol. 134:1787). There are four LHRs in the F (or A) allotype of ~250 kD, termed LHR-A, -B, -C, and -D, respectively, 5' to 3' (Wong, et al., 1989, J. Exp. Med. 169:847). While the first two SCRs in LHR-A determine its ability to bind C4b, the corresponding units in LHR-B and -C determine their higher affinities for C3b. The larger S (or B) allotype of ~290 kd has a fifth LHR that is a chimera of the 5' half of LHR-B and the 3' half of LHR-A and is predicted to contain a third C3b binding site (Wong, et al., 1989, J. Exp. Med. 169:847). The smallest F' (or C) allotype of CR1 of ~210 kD, found in increased incidence in patients with SLE and associated with patients in multiple lupus families (Dykman, et al., 1984, J. Exp. Med. 159:691; Van Dyne, et al., 1987, Clin. Exp. Immunol. 68:570), may have resulted from the deletion of one LHR and may be impaired in its capacity to bind efficiently to immune complexes coated with complement fragments.

A naturally occurring soluble form of CR1 has been identified in the plasma of normal individuals and certain individuals with SLE (Yoon, et al., 1985 J. Immunol. 134:3332–3338). Its structural and functional characteristics are similar to those of erythrocyte (cell surface) CR1, both structurally and functionally. Hourcade, et al. (1988, J. Exp. Med. 168:1255–1270) also observed an alternative polyadenylation site in the human CR1 transcriptional unit that was predicted to produce a secreted form of CR1 containing C4b binding domain.

Several soluble fragments of CR1 have also been generated via recombinant DNA procedures by eliminating the transmembrane region from the DNAs being expressed (Fearon, et al., Intl. Patent Publ. WO 89/09220, Oct. 5, 1989; Fearon, et al., Intl. Patent Publ. WO 91/05047, Apr. 18, 1991). The soluble CR1 fragments were functionally active, bound C3b and/or C4b and demonstrated factor I cofactor activity, depending upon the regions they contained. Such constructs inhibited in vitro the consequences of complement activation such as neutrophil oxidative burst, complement mediated hemolysis, and C3a and C5a production. A soluble construct sCR1/pBSCR1c, also demonstrated in vivo activity in a reversed passive Arthus reaction (Fearon, et al., 1989, supra; Fearon, et al., 1991, supra; Yeh, et al., 1991 supra), suppressed post ischemic myocardial inflammation and necrosis (Fearon, et al., 1989, supra; Fearon, et al., 1991, supra; Weismen, et al., 1990, Science, 249:146–151) and extended survival rates following transplantation (Pruitt and Bollinger, 1991, J. Surg. Res. 50: 350; Pruitt, et al., 1991, Transplantation 52:868).

CR2. Complement receptor type 2 (CR2, CD21) is a transmembrane phosphoprotein consisting of an extracellular domain which is comprised of 15 or 16 SCR's, a 24 amino acid transmembrane region, and a 34 amino acid cytoplasmic domain (Moore, et al., 1987, Proc. Natl. Acad. Sci. U.S.A. 84:9194–9198; Weis, et al., 1988, J. Exp. Med. 167:1047–1066. Electron microscopic studies of soluble recombinant CR2 have shown that, like CR1, it is an extended highly flexible molecule with an estimated contour length of 39.6 nanometers by 3.2 nanometers, in which each SCR appears as a ringlet 2.4 nanometers in length (Moore, et al., 1989, J. Biol. Chem. 34:20576–20582).

By means of recombinant DNA experiments with eukaryotic expression vectors expressing deletion or substitution mutants of CR2 in COS cells, the ligand binding sites of CR2 have been localized to the two N-terminal SCR's of the molecule (Lowell, et al., 1989, J. Exp. Med. 170:1931–1946). Binding by cell surface CR2 of the multivalent forms of C3 ligands such as iC3b and C3dg causes activation of B-cells (Melchers, et al., 1985, Nature, 317:264–267; Bohnsack, et al., 1988, J. Immunol. 141:456–463; Carter, et al., 1988, J. Immunol. 143:1755–1760).

A form of recombinant soluble CR2 has been produced (Moore, et al., 1989, J. Biol. Chem. 264:20576–20582). In analogy to the soluble CR1 system, soluble CR2 was produced in a recombinant system from an expression vector containing the entire extracellular domain of the receptor, but without the transmembrane and cytoplasmic domains. This recombinant CR2 is reported to bind to C3dg in a 1:1 complex with Kd equal to 27.5 mM and to bind to the Epstein-Bar proteins gp350/220 in a 1:1 complex with Kd=3.2 nM (Moore, et al., 1989, J. Viol. Chem. 264:20576–20582).

CR3. A third complement receptor, CR3, also binds iC3b. Binding of iC3b to CR3 promotes the adherence of neutrophils to complement-activating endothelial cells during inflammation (Marks, et al., 1989, Nature 339:314). CR3 is also involved in phagocytosis, where particles coated with iC3b are engulfed by neutrophils or by macrophages (Wright, et al., 1982, J. Exp. Med. 156:1149; Wright, et al., 1983, J. Exp. Med. 158:1338).

CR4. CR4 (CD11) also appears to be involved in leukocyte adhesion (Kishimoto, et al., 1989, Adv. Immunol. 46:149–82).

Abnormalities of CR1 in Human Disease

Diminished expression of CR1 on erythrocytes of patients with systemic lupus erythematosus (SLE) has been reported by investigators from several geographic regions, including Japan (Miyakawa, et al., 1981, Lancet 2:493–497; Minota, et al., 1984, Arthr. Rheum. 278:1329–135), the United States (Iida, et al., 1982, J. Exp. Med. 155:1427–1438; Wilson, et al., 1982, N. Engl. J. Med. 307:981–986) and Europe (Walport, et al., 1985, Clin. Exp. Immunol. 59:547; Jouvin, et al., 1986, Complement 3:88–96; Holme, et al., 1986, Clin. Exp. Immunol. 63:41–48). CR1 number has also been found to correlate inversely with serum levels of immune complexes, with serum levels of C3d, and with the amounts of erythrocyte-bound C3dg, perhaps reflecting uptake of complement-activating immune complexes and deposition on the erythrocyte as an "innocent bystander" (Ross, et al., 1985, J. Immunol. 135:2005–2014; Holme, et al., 1986, Clin. Exp. Immunol. 63:41–48; Walport, et al., 1985, Clin. Exp. Immunol. 59:547).

Abnormalities of complement receptor expression in SLE are not limited to erythrocyte CR1. Relative deficiencies of total cellular CR1 of neutrophils and plasma membrane CR1 of B lymphocytes of the SLE patients have been shown to occur (Wilson, et al., 1986, Arthr. Rheum. 29:739747).

The relative loss of CR1 from erythrocytes has also been observed in patients with Human Immunodeficiency Virus (HIV) infections (Tausk, F. A., et al., 1986, J. Clin. Invest. 78:977–982) and with lepromatous leprosy (Tausk, F. A., et al., 1985, J. Invest. Dermat. 85:58s–61s).

Complement activation has also been associated with disease states involving inflammation. The intestinal inflammation of Crohn's disease is characterized by the lymphoid infiltration of mononuclear and polymorphonuclear leukocytes. It was found recently (Ahrenstedt, et al., 1990, New Engl. J. Med. 322:1345–9) that the complement C4 concentration in the jejunal fluid of Crohn's disease patients increased compared to normal controls. Other disease states implicating the complement system in inflammation include thermal injury (burns, frostbite) (Gelfand, et al., 1989, Surgery 106:52–9), hemodialysis (Deppisch, et al., 1990, Kidney Inst. 37:696–706; Kojima, et al., 1989, Nippon Jenzo Gakkai Shi 31:91–7), and post pump syndrome in cardiopulmonary bypass (Chenoweth, et al., 1981, Complement Inflamm. 3:152–165; Chenoweth, et al., 1986, Complement 3:152–165; Salama, et al., 1988, N. Engl. J.

Med. 318:408–14). Both complement and leukocytes are reported to be implicated in the pathogenesis of adult respiratory distress syndrome (Zilow, et al., 1990, Clin Exp. Immunol. 79:151–57; Langlois, et al., 1989, Heart Lung 18:71–84). Activation of the complement system is suggested to be involved in the development of fatal complication in sepsis (Hack, et al., 1989, Am. J. Med. 86:20–26) and causes tissue injury in animal models of autoimmune diseases such as immune complex-induced vasculitis (Cochrane, 1984, Sringer Seminar Immunopath. 7:263), glomerulonephritis (Couser et al, 1985, Kidney Inst. 29:879), hemolytic anemia (Schreiber and Frank, 1972, J. Clin. Invest. 51:575), myasthenia gravis (Lennon, et al., 1978, J. Exp. Med. 147:973; Biesecker and Gomez, 1989, J. Immunol. 142:2654), type II collagen-induced arthritis (Watson and Townes, 1985, J. Exp. Med. 162:1878), and experimental allergic and hyperacute xenograft rejection (Knechtle, et al., 1985, J. Heart Transplant 4(5):541; Guttman, 1974, Transplantation 17:383; Adachi, et al., 1987, Trans. Proc. 19(1):1145). Complement activation during immunotherapy with recombinant IL-2 appears to cause the sever toxicity and side effects observed from IL-2 treatment (This, et al., 1990, J. Immunol. 144:2419).

Complement may also play a role in diseases involving immune complexes. Immune complexes are found in many pathological states including but not limited to autoimmune diseases such as rheumatoid arthritis or SLE, hematologic malignancies such as AIDS (Taylor, et al., 1983, Arthritis Rheum. 26:736–44; Inada, et al., 1986, AIDS Research 2:235–247) and disorders involving autoantibodies and/or complement activation (Ross, et al., 1985, J. Immunol. 135:2005–14).

Soluble Cr1 has been successfully used to inhibit complement activation in a number of animal models: Moat, B. P., et al., 1992, Amer. Review of Respiratory disease 145:A845; Mulligan, M. S., et al., 1992, J. Immunol. 148:1479–1485; Yeh, C. G. et al., 1991, J. Immunol. 146 250 . 256; Weisman, et al., 1990, Science 249:146–51; Pruitt, et al., 1991, Transplantation 52(5):868–73; Pruitt and Bollinger, 1991, J. Surg. Res. 50:350–55; Rabinovici, et al., 1992, J.Immunol. 149:1744–50.

Studies of Weisman et al (1990, Science 249:146–151) have demonstrated that sCR1 can prevent 90% of the generation of C3a and C5a in human serum activated by the yeast cell wall component zymosan. Weisman, et al. (1990, supra) also utilized sCR1 in the rat to inhibit complement activation and reduce the damage due to myocardial infarction. sCR1 also appears to inhibit the complement dependent process of the reverse Arthus reaction (Yeh, et al., 1991, J. Immuno. 146:250–256), and hyperacute xenograft rejection (Pruitt, et al., 1991, Transplantation 52:868–873). recent data (Moat, et al., 1992, Amer. Rev. Respiratory Disease 145:A845) indicate that sCR1 is of value in preventing complement activation in an experimental model of cardiopulmonary bypass in the pig, a situation where complement activation has been; demonstrated.

Currently, parenteral administration via intravenous, intramuscular or subcutaneous injection is the preferred route of administration to animals, and has been the only practical way to deliver therapeutically effective amounts of sCR1 systemically.

The Uncertain Role of Complement in Lung Injury

Several models have been used to study the role of complement in acute inflammatory injury (Mulligan, M. S., et al., 1992, J. Immunol., 148:1479–1485). Intrapulmonary deposition of either IgG or IgA immune complexes in rats leads to acute lung injury with damage to both vascular endothelial as well as alveolar epithelial cells (Mulligan, M. S., et al., 1992, J. Immunol., 148:3086–3092). Experimental models suggest that in immune-complex induced lung injury, complement is necessary for the full development of injury (Mulligan, M. S., 1992 supra). Complement inhibition results in decreased severity of remote pulmonary injury caused by intestinal ischemia (Hill, et al., 1992, J. Immunol. 149:5, 1723–1728).

Smoke inhalation injury is a significant comorbid factor in major thermal burn trauma. Noxious chemicals generated in incomplete combustion not only directly injury the exposed airways, but also may activate chemotactic factors which could result in leukocyte activation and prostanoid production. Activated polymorphonuclear leukocytes are considered as significant effectors in the progressive airway inflammation following smoke inhalation (Basadre, et al., 1988, surg. 104:208–215). The airway damage with subsequent pulmonary edema worsens oxygenation in the lung and increases the susceptibility to pulmonary infection, which enhances morbidity and mortality. Though physiologic changes following cigarette smoking have been suggested to depend on complement activation (Robbins et al, 1991, Am. J. Physiol. 260:L254–9; Kobayashi, et al., 1988, Arch. Env. Health 43:371–4; Kew, et al., 1987, Clin, Immunol. Immunopath. 43:73–81), the role of complement activation in smoke inhalation injury has not been clarified. Moreover, a previous study has shown that pretreatment with cobra venom factors did not alleviate lung injury following smoke inhalation, and compromised the defense mechanism of the lung in an ovine model (Shimazu et al., 1988, U.S. Army Inst. for Lung. Res. Ann. Res. progress Report for FY 1988, pp. 276–87). Cobra venom factors, which activate and deplete complement, also induced transient hypoxemia and pulmonary hypertension.

Studies investigating complement system activation have been hampered by the lack of the appropriate tools to manipulate the complement system. Numerous studies in the past have utilized the reagent Cobra Venom Factor (CVF) to activate the complement system and in this manner deplete an animal of intact complement components and render the complement system inoperative. However, in the process of depleting the complement system with CVF, massive activation of the system occurs, accompanied by the elaboration of all of the biologically active products of complement system activation such as C3b, the anaphylatoxins C3a and C5a and the Membrane Attack Complex (Goldstein, "Complement: biologically active products" In *Inflammation, Basic Principles and Clinical Correlates, 2nd Ed.,* Galin, et al. (eds.), Raven Press: New York, 1992). The data from such experiments are unreliable since the observed effects may be due to the prior activation of the complement system rather than the fact that the complement system was inoperative. Therefore interpretation of these experiments with CVF is uncertain, and there is no reliable way to evaluate the role of complement in the aforementioned models, or in other conditions, such as anaphylaxis.

Aerosolization of Protein Therapeutic Agents

Recently some attention has been directed to the delivery of protein and peptide drugs through noninvasive routes such as intranasal, gastrointestinal, or rectal absorption (Lee, V. H. L., 1988 Crit. Rev. Ther. Drug Carrier Syst., 5:69; Lee, V. H. L., 1990, J. Controlled Release, 13:213; Lee, V. H. L., Ed., Peptide and Protein Drug Delivery, Marcel Dekker, New York 1991; D Boer, A. G., et al., 1990, J. Controlled Release 13:241). Some studies have specifically focused on the fate of proteins delivered through the pulmonary route or during transit through the pulmonary circulation (Gillespie, M. N., et al., 1985, J. Pharm. Ther. 232:675; Braley, et al., 1978, J. Immunol. 121:926–929; Braley, et al., 1979, J. Clinical Invest. 63:1103–1109; Dansen, et al., 1979, Chest 75(2 Supt.):276–278,) Willoughby and Willoughby, 1977, J. Immunol 119:2137–2146; Willoughby, et al., 1979, Lab Invest. 40:399–414; and Shenkin, et al., 1980, J. Immunol. 124: 1763–1772).

In part, these studies in the area of pulmonary delivery of proteins have lead to the development of formulations for liquid aerosols to deliver larger bioative proteins via nebulization (Hubbard, R. C., et al., 1989, Annals. Int. Med., 111:206; Oeswein, J. and Patteon, J., 1990, Aerozolization of Proteins, Proceedings of Symposium on Respiratory Drug Delivery II, Keystone Co., ; Debs, R. J., et al., 1988, J. Immunol. 140:3482). For instance, recombinant human growth factor has been delivered via a nebulizer to rats and bioavailability assessed by measurement of growth rate (Oeswein, 1990, supra). Hubbard, et al., supra, showed that pulmonary delivery of $\alpha$-antitrypsin is effective to achieve access to the systemic circulation. Additionally, aerosol inhalation to deliver insulin has been reported to be an effective therapeutic formulation for diabetes mellitus (Wigley, F. M., 1971, Diabetes 20:552)

Citation or identification of any reference in Section 2 of this application shall not be construed as an admission that such reference is available as prior art to the present invention.

SUMMARY OF THE INVENTION

The present invention relates to pulmonary administration of a complement inhibitory protein by inhalation for the therapeutic treatment of diseases or disorders involving complement. More particularly, the invention is directed to pulmonary administration of complement receptor 1 (CR1) by inhalation. Thus, the present invention provides an aerosol formulation comprising an amount of a complement inhibitory protein, and more particularly a CR1 protein, effective to inhibit complement and a dispersant. In one embodiment, the complement inhibitory protein, or more particularly, the CR1 protein, can be provided in a liquid aerosol formulation. Alternatively, the complement inhibitory protein, or more particularly, the CR1 protein, can be provided as a dry powder aerosol formulation. In a preferred embodiment, the CR1 is soluble CR1 (sCR1).

The term "complement inhibitory protein" as used herein includes fragments, derivatives and analogs of such complement inhibitory proteins as are known in the art, provided such fragments, derivatives or analogs have complement inhibitory activity.

Furthermore, the present invention is directed to a method for treating a systemic disease or disorder involving complement comprising pulmonary administration of an amount of a complement inhibitory protein effective to inhibit systemic complement activity to a subject suffering from a disease or disorder involving complement. The present invention further provides a method for treating a lung disease or lung disorder involving complement comprising pulmonary administration of an amount of a complement inhibitory protein effective to inhibit complement activity to a subject suffering from the lung disease or lung disorder involving complement.

The present invention further provides a method for treating anaphylaxis comprising administering an amount of a complement inhibitory protein effective to inhibit complement activity to a subject suffering anaphylaxis. In one embodiment, the administration of the complement inhibitory protein can be parenteral. More preferably, the administration of the complement inhibitory protein can be pulmonary. Pulmonary administration is particularly indicated for treatment of bronchoconstriction associated with anaphylaxis.

The present invention still further provides a method for treating bronchoconstriction comprising administering an amount of a complement inhibitory protein effective to inhibit complement activity to a subject suffering bronchoconstriction. In one embodiment, the administration of the complement inhibitory protein can be parenteral. More preferably, the administration of the complement inhibitory protein can be pulmonary. Pulmonary administration is particularly indicated for treatment of bronchoconstriction associated with anaphylaxis, asthma, or other lung irritation or insult.

The present invention is based on the important and surprising discovery that a complement inhibitory protein administered to a subject can modulate complement-related effects of a disorder or disease involving the lung. This discovery led to recognition that pulmonary administration of a complement inhibitory protein, i.e., administration directly to the lung, can result in beneficial effects in the extravascular space, as well as systemic effects.

The present invention is further based in part on the discovery that complement activation is involved in anaphylaxis, and the anaphylactic symptoms of bronchoconstriction and blood pressure changes (hypotension).

It is yet another discovery of the present invention that a complement inhibitory protein can attenuate or prevent bronchoconstriction.

A particular advantage of the present invention is that inhalation therapy is convenient, because it does not involve controlled devices such as syringes, and is fast and generally agreeable. Another advantage of the present invention is that the complement inhibitory protein can e self administered. This is important, since often a subject in need of complement inhibitory therapy is not near to trained medical personnel who could administer the complement inhibitory protein parenterally. Such situations occur, for example, in anaphylaxis due to antigen, and more particularly, allergen exposure; in industries with a likelihood of exposure to dusts and minerals such as silicon, coal dust, beryllium and asbestos; in industries or occupations with a likelihood of exposure to caustic chemicals and gasses such as chlorine, phosgene, sulfur dioxide, hydrogen sulfide, nitrogen dioxide, ammonia and hydrochloric acid; and for firefighters who risk lung tissue damage from inhalation of smoke or hot air.

It is a further advantage of the present invention that the subjects at risk for injury that involves the complement system can use the formulations of the present invention, which comprise a complement inhibitory protein, preferably a CR1 protein, prophylactically. It is demonstrated in an example, infra, that prophylactic administration of a complement inhibitory protein to a subject has no or minimal deleterious effects, and substantially protects the subject from complement-associated injury.

The invention therefore provides for the therapeutic and prophylactic treatment of complement related diseases or disorders, particularly complement related diseases or disorders of the lung, with complement receptor proteins and analogues or derivatives thereof.

In a particular embodiment, the present inventors have discovered that soluble complement receptor type 1 is effective is reducing the bronchoconstriction, hypotension and decrease in circulating platelet count seen in anaphylaxis.

Thus, according to the present invention, formulations are provided which provide an effective noninvasive alternative to other parenteral routes of administration of sCR1. Delivery of complement receptor proteins can be accomplished in the lung via aerosolization and subsequent inhalation.

The invention can be practiced by using any complement receptor protein, or fragment, derivative or analog thereof, including soluble complement receptor. In a preferred embodiment of the present invention, the complement inhibitory protein is Cr1, and more preferably, soluble CR1 (sCR1). Most preferably, the soluble CR1 protein has the characteristics of the protein expressed by a Chinese hamster ovary cell DUX B11 carrying plasmid pBSCR1/pTCSgpt as deposited with the ATCC and assigned accession number CRL 10052.

BRIEF DESCRIPTION OF THE FIGURES

FIGS. 1A–F. Effect of 15 mg/kg sCR1 on the ovalbumin-induced changes in pulmonar compliance (A,D), airway resistance (B,E) and systemic blood pressure (C,E) in passively (Experimental Group 1; A–C) or actively (Experimental Group 2; D–F) sensitized guinea pigs. Ovalbumin was administered intravenously at time 0 at a dose of 176 μg/kg or 300 μg/kg for passively sensitized and actively sensitized animals, respectively. Values represent the mean ±S.E. of the response in 4 to 5 different animals pretreated with either PBS (vehicle) or sCR1. *p<0.05 over the time interval indicated.

FIGS. 2A–D. Effect of 15 mg/kg sCR1 on ovalbumin-induced changes in circulating white blood cells (A,C) or platelets (B,D) in passively (Experimental Group 1; A and B) or actively (Experimental Group 2; C and D) sensitized guinea pigs. Values represent the mean ±S.E. of determinations in 3 to 5 different animals. An asterick (*) represents a statistically significant difference (p<0.05) in the antigen-induced change in circulating cells in sCR1 treated animals compared to PBS (vehicle) treated animals.

FIGS. 6A–B. Effect of a cumulative dose of 105 mg/kg sCR1 on the response of the guinea pig to histamine (Experimental Group 4). Values represent the mean ±S.E. of compliance (A) and resistance (B) determinations in 4 animals, pretreated with either PBS (vehicle) or sCR1 prior to bovine serum albumin challenge and evaluation of the histamine responsiveness.

DETAILED DESCRIPTION OF THE INVENTION

Figure 3A:
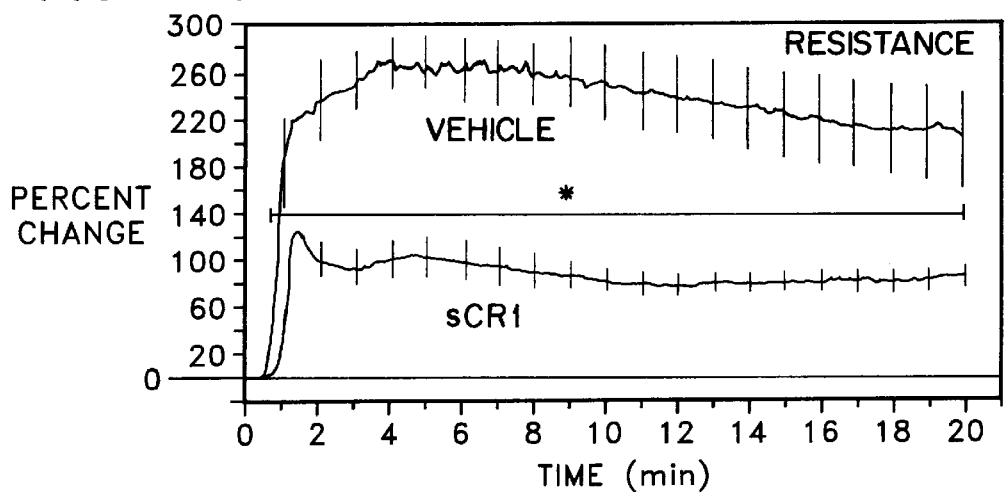
FIGS. 3A–C. Effect of a cumulative dose of 105 mg/kg sCR1 on the ovalbumin-induced changes in pulmonary compliance (A), airway resistance (B) and systemic blood pressure (C) in actively sensitized guinea pigs (Experimental Group 3). Ovalbumin was administered intravenously at time 0 at a dose of 2 mg/kg. Values represent the mean ±S.E. of the response to ovalbumin in 9 animals pretreated with either PBS (vehicle) or sCR1. An asterick (*) indicates *p<0.05 over the time interval indicated.

The present invention relates to a method for treating diseases and disorders related to systemic complement activation by the administration of complement inhibitory proteins, or fragments, derivatives or analogs thereof, which complement inhibitory proteins have the effect of inhibiting at least one activity associated with complement activation, via the pulmonary route. The invention further provides for the treatment of complement related lung disorders via the direct administration of complement inhibitory proteins to the airways. In specific embodiments, the invention provides for the treatment of complement related disorders by direct administration of soluble complement receptor protein to the lung via inhalation of sCR1. The invention also provides for the treatment of bronchoconstriction or anaphylaxis, or both, via administration of sCR1 parenterally or by inhalation.

The present inventors have discovered that administration of soluble complement receptor type 1 to actively sensitized guinea pigs results in an inhibition of antigen-induced decrease in dynamic lung compliance and increase in pulmonary vascular resistance. Administration of sCR1 also shortens the hypertensive response to antigen challenge and eliminates the hypotensive response. Thus the present inventors have shown that complement is essential to the bronchoconstriction and changes in blood pressure associated with anaphylaxis.

Furthermore, these studies demonstrate that important complement activation is occurring at extravascular sites, which are readily accessible to pulmonary administration of sCR1. The present inventors therefore provide for the direct administration of complement receptor proteins to the lung, which are an effective in treating both the local and systemic effects of inappropriate complement activation.

In one embodiment, the present invention provides for the treatment of complement related lung disorders via the pulmonary route. Formulations are provided which are an effective noninvasive alternative to the systemic administration of sCR1. Delivery of complement receptor proteins can be accomplished in the lung via aerosolization and subsequent inhalation.

The invention can be practiced by using any complement receptor protein fragment or derivative thereof including soluble complement receptor. In a preferred embodiment of the present invention, the protein backbone of the sCR1 contains the LHR-A, LHR-B, LHR-C, LHR-D, SCR29, and SCR30 regions up to and including the first alanine residue of the transmembrane region. In another embodiment of the present invention the sCR1 protein described above lacks the LHR-A region.

Thus the present invention provides therapeutic and prophylactic formulations of complement inhibitory proteins that are useful in the treatment of complement related diseases or disorders. The methods and formulations of the invention are described in detail below.

As used herein, the term "pulmonary administration" refers to administration of a formulation of the invention through the lungs by inhalation.

As used herein, the term "inhalation" refers to intake of air to the alveoli. In specific examples, intake can occur by self-administration of a formulation of the invention while inhaling, or by administration via a respirator, e.g., to an patient on a respirator. The term "inhalation" used with respect to a formulation of the invention is synonymous with "pulmonary administration."

As used herein, the term "parenteral" refers to introduction of a complement inhibitory protein into the body by other than the intestines, and in particular, intravenous (i.v.), intraarterial (i.a.), intraperitoneal (i.p.), intramuscular (i.m.), intraventricular, and subcutaneous (s.c.) routes.

As used herein, the term "aerosol" refers to suspension in the air. In particular, aerosol refers to the particlization of a formulation of the invention and its suspension in the air. According to the present invention, an aerosol formulation is a formulation comprising a complement inhibitory protein that is suitable for aerosolization, i.e., particlization and suspension i the air, for inhalation or pulmonary administration.

As used herein, the term "systemic" refers to a disease or disorder, or original site of injury distant to the lung or involving the entire body of the organism. The term "local" therefore is used herein with respect to the lung.

A disease or disorder involving complement as used herein refers to a condition of inappropriate complement activation, e.g., resulting from an insult or injury. As used herein, the terms "disease" and "disorder" are used in their most general sense, and refer to any condition, illness, insult, injury, harm, pathological condition, or other term of art that implies a harmful or detrimental physiological condition. Generally complement activation accompanies or results from some other cause. Thus the present invention is directed to treatment or prophylaxis of the complement mediated component of a disease or disorder.

For the sake of clarity, the present invention is described in detail in sections relating to complement inhibitory proteins, aerosol formulations, and methods for treatment and prophylaxis.

Complement Inhibitory Proteins

Complement inhibitory proteins within the scope of this invention include any protein which is able to bind to and inhibit the function of a complement protein and inhibit complement activity. Such complement inhibitory proteins include but are not limited to: complement receptor type 1 (CR1), which is the receptor for complement components C3b and C4b; complement receptor type 2 (CR2), which is the receptor for C3d; complement receptor type 3 (CR3), the receptor for iC3b; complement receptor type 4 (CR4), which is specific to iC3b; complement receptor type 5 (CR5), which is specific for the C3d portion of iC3b, C3dg, and C3d; the C5a receptor (C5a-R); and receptors for C3a and C4a. In a preferred aspect, the invention is also meant to include those members of the family of complement regulatory proteins that contain the conserved short consensus repeat (SCR) motif. SCR motifs are found in complement receptor type 1 and in several other C3/C4-binding proteins, most notably CR2, factor H, C4-binding protein (C4-BP), membrane cofactor protein (MCP), and decay accelerating factor (DAF). The genes for factor H, C4-BP, CR2, and DAF map to a region on chromosome 1 which has been designated "regulators of complement activation" (RCA) (Hourcade, D., et al., 1989, Advances in Immunol., 45:381–416). Particular analogs of these regulators of complement activation are found in Atkinson, et al., EPO publication no. 0 512 733 A2, published on Nov. 11, 1992.

It will be appreciated by one of skill in the art that the form of the complement receptor protein, its analog or derivative is important in achieving pulmonary delivery. The present invention includes those forms of the complement inhibitory protein that are readily absorbed by tissues, that are protected from rapid metabolism and/or that provide for prolonged half life. Those modifications of protein formulation which may effect absorption include but are not limited to use of a prodrug, chemical modification of the primary structure, incorporation of the protein in a liposome or other encapsulation material, and coadministration of the complement inhibitory protein with a chemical absorption enhancer (Wearley, L. L., 1991, Crit. Rev. in Ther. Drug Carrier Systems, 8(4):333). In minimizing metabolism of the complement inhibitory protein and thereby increasing the effective amount of protein, such modifications may include chemical modifications as discussed supra, coadministration with an enzyme inhibitor, or covalent attachment to a polymer (Wearley, L. L., 1991, supra). Other modifications of proteins that can result in increased half-life or variations in absorbability include glycosylation, which can be affected by culture conditions in production of a recombinant protein (or avoided altogether by expression in bacteria), or by chemical or enzymatic modification of a protein that has been synthesized or expressed.

The present invention is particularly directed to the C3b/C4b receptor (CR1) protein. The CR1 gene and its encoded protein are provided for in International Patent Publication #WO 89/09220 published Oct. 5, 1989 and entitled "The human C3b/C4b receptor (CR1)".

Once the CR1 gene and its encoded protein are available any number of techniques known in the art can be used to modify the gene or its encoded protein. The invention is meant to include such CR1-related fragments, derivatives, and analogs. The CR1-related fragments, derivatives, and analogs for use in the formulations of the invention can be produced by various methods known in the art. The manipulations which result in their production can occur at the gene or protein level. For example, the cloned CR1 gene can be modified by any of numerous strategies known in the art (Maniatis, T., 1982, Molecular Cloning, A Laboratory Manual, Cold Spring Harbor Laboratory, Cold Spring Harbor, N.Y.). The CR1 sequence can be cleaved at appropriate sites with restriction endonuclease(s), followed by further enzymatic modification if desired, isolated, and ligated in vitro. In the production of the gene encoding a derivative, analogue, or peptide related to CR1, care should be taken to ensure that the modified gene remains within the same translational reading frame as CR1, uninterrupted by translational stop signals, in the gene region where the desired CR1-specific activity is encoded.

Additionally, the CR1 gene can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551), use of TABX linkers (Pharmacia), etc.

Manipulations of the CR1 sequence may also be made at the protein level. Any of numerous chemical modifications may be carried out by known techniques, including but not limited to specific chemical cleavage by cyanogen bromide, trypsin, chymotrypsin, papain, V8 protease, NaBH4; acetylation, formylation, oxidation, reduction, metabolic synthesis in the presence of tunicamycin, etc.

Specific modifications of the nucleotide sequence of CR1 can be made by recombinant DNA procedures that result in sequences encoding a protein having multiple LHR-B sequences. See, e.g., International Patent Publication WO 91/05047, published Apr. 18, 1991. Such valency modifications alter the extent of C3b binding disorders associated with such functions, such as immune or inflammatory disorders. For example, full-length CR1 or fragments thereof and related molecules which exhibit the desired activity can have therapeutic uses in the inhibition of complement by their ability to act as a factor I cofactor, promoting the irreversible inactivation of complement components C3b or C4b (Fearon, D. T., 1979, Proc. Natl. Acad. Sci. U.S.A. 76:5867; Iida, K. and Nussenzweig, v., 1981, J. Exp. Med. 153:1138), and/or by the ability to inhibit the alternative or classical C3 or C5 convertases.

Portions of the sequences of CR1 that contain specific well defined combinations of LHRs or SCRs can also be generated. The activities of these compounds can be predicted by choosing those portions of the full-length CR1 molecules that contain a specific activity. The resulting fragments should contain at least one of the functions of the parent molecule. Such functions include but are not limited to binding of C3b and/or C4b, in free or in complex forms, promotion of phagocytosis, complement regulation, immune stimulation, ability to act as a factor I cofactor, promoting the irreversible inactivation of complement components C3b or C4b, (Fearon, D. T., 1979, Proc. Natl. Acad. Sci. U.S.A. 76:5867; Iida, K. and Nussenweig, V., 1981, J. Exp. Med. 153:1138), effect immune complex clearance and/or by the ability to inhibit the alternative or classical C3 or C5 convertases.

In addition, analogues and peptides related to CR1 can be chemically synthesized. For example, a peptide corresponding to a portion of CR1 which mediates the desired activity (e.g., C3b and/or C4b binding, immune stimulation, complement regulation, etc.) can be synthesized by use of a peptide synthesizer.

In a particular embodiment, nucleic acid sequences encoding a fusion protein, consisting of a molecule comprising a portion of the CR1 sequence plus a non-CR1 sequence, can be produced. See, e.g., International Patent Publication No. WO 91/05047. Thus further modifications of CR1 include the generation of chimeric molecules containing portions of the CR1 LHR or SCR sequences attached to other molecules whose purpose is to affect solubility, pharmacology or clearance of the resultant chimeras. Such chimeras can be produced either at the gene level as fusion proteins or at the protein level as chemically produced derivatives. Chimeric molecules comprising portions of immunoglobulin chains can contain Fab or $(Fab')_2$ molecules, produced by proteolytic cleavage or by the introduction of a stop codon after the hinge region in the heavy chain to delete the $F_c$ region of a non-complement activating isotype in the immunoglobulin portion of the chimeric protein to provide $F_c$ receptor-mediated clearance of the complement activating complexes. Other molecules that may be used to form chimeras include, but are not limited to, proteins such as serum albumin, heparin, or immunoglobulin, polymers such as polyethylene glycol or polyoxyethylated polyols, or proteins modified to reduce antigenicity by, for example, derivatizing with polyethylene glycol. Suitable molecules are known in the art and are described, for example, in U.S. Pat. Nos. 4,745,180, 4,766, 106 and 4,847,325 and references cited therein. Additional molecules that may be used to form derivatives of the biological compounds or fragments thereof include protein A or protein G (International Patent Publication WO 87/05631 published Sep. 24, 1987 and entitled "Method and means for producing a protein having the same IgG specificity as protein G"; Bjorck, et al., 1987, Mol. Immunol. 24:1113–1122; Guss, et al., 1986, EMBO J. 5:1567–1575; Nygren, et al., 1988, J. Molecular Recognition 1:69–74).

The CR1 proteins may be isolated and purified by standard methods including chromatography (e.g., ion exchange, affinity, and sizing column chromatography, high performance liquid chromatography), centrifugation, differential solubility, or by any other standard technique for the purification of proteins. If the complement receptor protein is exported by a cell that is producing it, a particularly efficacious method for purification of the protein is as follows: the cell culture medium containing protein is subject to the sequential steps of a) cationic exchange chromatography, b) ammonium sulfate precipitation, c) hydrophobic interaction chromatography, d) anionic exchange chromatography, e) further cationic exchange chromatography and f) size exclusion chromatography.

In a preferred embodiment, the instant invention relates to soluble CR1 molecules. As used herein the term soluble CR1 molecules means portions of the CR1 protein which upon expression are not located in the cell surface as membrane proteins. As a particular example, CR1 molecules which substantially lack the transmembrane region are soluble CR1 molecules. In a specific embodiment of the invention, an expression vector can be constructed to encode a CR1 molecule which lacks the transmembrane region (e.g., by deletion carboxyl-terminal to the arginine encoded by the most C-terminal SCR), resulting in the production of a soluble CR1 fragment. In one embodiment, such a fragment can retain the ability to bind C3b and/or C4b, in free or in complex forms. In a particular embodiment, such a soluble CR1 protein no longer exhibit factor I cofactor activity.

Soluble constructs carrying some or all of the binding sites of CR1 are also envisioned. Such constructs will inhibit activation of complement and the complement dependent activation of cells. For example, in a specific embodiment, a soluble CR1 molecule can be used which retains a desired functional activity, as demonstrated, e.g., by the ability to inhibit classical complement-mediated hemolysis, classical C5a production, classical C3a production, or neutrophil oxidative burst in vitro. In one embodiment such a fragment can retain the ability to bind C3b and/or C4b, in free or in complex form. The sCR1 molecule so produced can contain the LHR-A, LHR-B, LHR-C, LHR-D, SCR29, SCR30, up to and including the first alanine residue of the transmembrane region. In a preferred aspect of the invention, the soluble CR1 protein has the characteristics of the protein expressed by a Chinese hamster ovary cell DUX B11 carrying plasmid pBSCR1/pTCSgpt as deposited with the ATCC and assigned accession number CRL 10052.

In a further specific embodiment a CR1 molecule can be produced that lacks the LHR-A region of the CR1 molecule. To this end, an expression vector can be constructed to encode a CR1 molecule which lacks the transmembrane region and SCRs 1–7, resulting in the production of a soluble CR1 fragment that would be expected to inhibit the alternative pathway preferentially.

Soluble complement receptor type 1 (sCR1) and processes by which it can be prepared are disclosed in International Patent Publication WO 89/09220 (Oct. 5, 1989) and WO 91/05047 (Apr. 18, 1991).

Once the soluble CR1 expression vector and gene product provided for above are available any number of techniques can be used to isolate and purify the soluble CR1 protein.

The complement inhibitory proteins of the invention can be assayed by techniques known in the art in order to demonstrate their complement inhibiting activity. Such assays include but are not limited to the following in vitro tests for the ability to inhibit complement activity or to selectively inhibit the generation of complement-derived peptides:

(i) measurement of inhibition of complement-mediated lysis of red blood cells (hemolysis)

(ii) measurement of ability to inhibit formation of C5a and C5a des Arg and/or measurement of ability to inhibit formation of C3a or C3a des Arg.

Any complement inhibitory protein, or fragment, derivative or analog thereof, in particular a CR1 protein, that has any one of the activities associated with complement receptors is within the scope of this application. Activities normally associated with complement receptor type 1 are well documented in the art and include but are not limited to those activities and assays described in International Patent Application number PCT/US89/01358, published Oct. 5, 1989 as WO89/09220 and entitled "The Human C3b/C4b Receptor (CR1)"; Weissman, et al., 1990, Science 249:146–151; Fearon, D. T. and Wong, W. W., 1989, Ann. Rev. Immunol. 1:243; Fearon, D. T., 1979, Proc. Natl. Acad. Sci. U.S.A. 76:5867; Iida, K. and Nussenzweig, V., 1981, J. Exp. Med. 153:1138; Klickstein et al., 1987, J. Exp. Med., 165:1095; Weiss, et al., 1988, J. Esp. Med. 167:1047–1066; Moore, et al., 1987, Proc. Natl. Acad. Sci. 84:9194; Moore, et al, 1989, J. Biol. Chem. 264:205–76). For example, for soluble CR1 proteins, such activities include the abilities in vitro to inhibit neutrophil oxidative burst, to inhibit complement-mediated hemolysis, to inhibit C3a and/or C5a production, to bind C3b and/or C4b, to exhibit factor I cofactor activity, and to inhibit C3 and/or C5 convertase activity.

Pulmonary Delivery of Complement Receptor Proteins

The present invention contemplates formulations comprising a complement inhibitory protein for use of a wide variety of devices that are designed for the delivery of pharmaceutical compositions and therapeutic formulations to the respiratory tract. The preferred route of administration of the present invention is in the aerosol or inhaled form. The complement inhibitory proteins of the present invention, combined with a dispersing agent, or dispersant, can be administered in an aerosol formulation as a dry powder or in a solution or suspension with a diluent.

As used herein, the term "dispersant" refers to a agent that assists aerosolization of the protein or absorption of the protein in lung tissue, or both. Preferably the dispersant is pharmaceutically acceptable. As used herein, the term "pharmaceutically acceptable" means approved by a regulatory agency of the Federal or a state government as listed in the U.S. Pharmacopeia or other generally recognized pharmacopeia for use in animals, and more particularly in humans. Suitable dispersing agents are well known in the art, and include but are not limited to surfactants and the like. For example, surfactants that are generally used in the art to reduce surface induced aggregation of the protein caused by atomization of the solution forming the liquid aerosol may be used. Nonlimiting examples of such surfactants are surfactants such as polyoxyethylene fatty acid esters and alcohols, and polyoxyethylene sorbitan fatty acid esters. Amounts of surfactants used will vary, being generally within the range or 0.001 and 4% by weight of the formulation. In a specific aspect, the surfactant is polyoxyethylene sorbitan monooleate or sorbitan trioleate. Suitable surfactants are well known in the art, and can be selected on the basis of desired properties, depending on the specific formulation, concentration of complement inhibitory protein, diluent (in a liquid formulation) or form of powder (in a dry powder formulation), etc.

Moreover, depending on the choice of the complement inhibitory protein, the desired therapeutic effect, the quality of the lung tissue (e.g., diseased or healthy lungs), and numerous other factors, the liquid or dry formulations can comprise additional components, as discussed further below.

The liquid aerosol formulations contain the complement inhibitory protein and a dispersing agent in a physiologically acceptable diluent. The dry powder aerosol formulations of the present invention consist of a finely divided solid form of the complement inhibitory protein and a dispersing agent. With either the liquid or dry powder aerosol formulation, the formulation must be aerosolized. That is, it must be broken down into liquid or solid particles in order to ensure that the aerosolized dose actually reaches the alveoli. In general the mass median dynamic diameter will be 5 micrometers or less in order to ensure that the drug particles reach the lung alveoli (Wearley, L. L., 1991, 1991, Crit. Rev. in Ther. Drug Carrier Systems 8:333). The term "aerosol particle" is used herein to describe the liquid or solid particle suitable for pulmonary administration, i.e., that will reach the alveoli. Other considerations such as construction of the delivery device, additional components in the formulation and particle characteristics are important. These aspects of pulmonary administration of a drug are well known in the art, and manipulation of formulations, aerosolization means and construction of a delivery device require at most routine experimentation by one of ordinary skill in the art.

With regard to construction of the delivery device, any form of aerosolization known in the art, including but not limited to nebulization, atomization or pump aerosolization of a liquid formulation, and aerosolization of a dry powder formulation, can be used in the practice of the invention. A delivery device that is uniquely designed for administration of solid formulations is envisioned. Often, the aerosolization of a liquid or a dry powder formulation will require a propellant. The propellant may be any propellant generally used in the art. Specific nonlimiting examples of such useful propellants are a chlorofluorocarbon, a hydrofluorocarbon, a hydochlorofluorocarbon, or a hydrocarbon, including trifluoromethane, dichlorodifluoromethane, dichlorotetrafluoroethanol, and 1,1,1,2-tetrafluoroethane, or combinations thereof.

In a preferred aspect of the invention, the device for aerosolization is a metered dose inhaler. A metered dose inhaler provides a specific dosage when administered, rather than a variable dose depending on administration. Such a metered dose inhaler can be used with either a liquid or a dry powder aerosol formulation. Metered dose inhalers are well known in the art.

Once the complement inhibitory protein reaches the lung, a number of formulation-dependent factors effect the drug absorption. It will be appreciated that in treating a complement related disease or disorder that requires circulatory levels of the complement inhibitory protein, such factors as aerosol particle size, aerosol particle shape, the presence or absence of infection, lung disease or emboli may affect the absorption of the protein. For each of the formulations described herein, certain lubricators, absorption enhancers, protein stabilizers or suspending agents may be appropriate. The choice of these additional agents will vary depending on the goal. It will be appreciated that in instances where local delivery of the complement inhibitory protein is desired or sought, such variables as absorption enhancement will be less critical.

In a further embodiment, an aerosol formulation of the present invention can include other active ingredients in addition to the complement inhibitory protein. In a preferred embodiment, such active ingredients are those used for the treatment of lung disorders. For example, such additional active ingredients include, but are not limited to, bronchodilators, antihistamines, epinephrine, and the like, which are useful in the treatement of asthma. In another embodiment, the additional active ingredient can be an antibiotic, e.g., for the treatment of pneumonia. In a preferred embodiment, the antibiotic is pentamidine.

In general, the complement inhibitory protein of the present invention, or the fragment or analog or derivative thereof is introduced into the subject in the aerosol form in an amount between 0.01 mg per kg body weight of the mammal up to about 100 mg per kg body weight of said mammal. In a specific embodiment, the dosage is dosage per day. One of ordinary skill in the art can readily determine a volume or weight of aerosol corresponding to this dosage based on the concentration of complement inhibitory protein in an aerosol formulation of the invention; alternatively, one can prepare an aerosol formulation which with the appropriate dosage of complement inhibitory protein in the volume to be administered, as is readily appreciated by one of ordinary skill in the art. It is also clear that the dosage will be higher in the case of inhalation therapy for a systemic disease or disorder involving complement, and lower for a lung disease or disorder involving complement, since the local concentration of complement inhibitory protein in the lung will be greater if the protein is administered to the lung. It is an advantage of the present invention that administration of a complement inhibitory protein directly to the lung allows use of a less complement inhibitory protein, thus limiting both cost and unwanted side effects.

The formulation may be administered in a single dose or in multiple doses depending on the disease indication. It will be appreciated by one of skill in the art the exact amount of prophylactic or therapeutic formulation to be used will depend on the stage and severity of the disease, the physical condition of the subject, and a number of other factors.

Systems of aerosol delivery, such as the pressurized metered dose inhaler and the dry powder inhaler are disclosed in Newman, S. P., *Aerosols and the Lung*, Clarke, S. W. and Davia, D. editors, pp. 197–22 and can be used in connection with the present invention.

It is particularly contemplated that a liposome formulation may be especially effective for administration of a complement inhibitory protein by inhalation. This is particularly so where long term administration is desired (See Wearley, 1991, Crit. Rev. in Ther. Drug Carrier Systems 8:333).

Liquid Aerosol Formulations

The present invention provides aerosol formulations and dosage forms for use in treating subjects suffering from a complement related disease or disorder. In general such dosage forms contain one or more complement inhibitory proteins, or fragment, derivatives or analogs thereof in a pharmaceutically acceptable diluent. Pharmaceutically acceptable diluents include but are not limited to sterile water, saline, buffered saline, dextrose solution, and the like. In a specific embodiment, a diluent that may be used in the present invention or the pharmaceutical formulation of the present invention is phosphate buffered saline, or a buffered saline solution generally between the pH 7.0–8.0 range, or water.

The liquid aerosol formulation of the present invention may include, as optional ingredients, pharmaceutically acceptable carriers, diluents, solubilizing or emulsifying agents, surfactants and excipients.

The liquid aerosol formulations of the present invention will typically be used with a nebulizer. The nebulizer can be either compressed air driven or ultrasonic. Any nebulizer known in the art can be used in conjunction with the present invention such as but not limited to: Ultravent, Mallinckrodt, Inc. (St. Louis, Mo.); the Acorn II nebulizer (Marquest Medical Products, Engelwood Colo.). Other nebulizers useful in conjunction with the present invention are described in U.S. Pat. Nos. 4,624,251 issued Nov. 25, 1986; 3,703,173 issued Nov. 21, 1972; 3,561,444 issued Feb. 9, 1971 and 4,635,627 issued Jan. 13, 1971.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for protein stabilization or for the regulation of osmotic pressure. Examples of the agents include but are not limited to salts, such as sodium chloride, or potassium chloride, and carbohydrates, such as glucose, galactose or mannose, and the like.

Aerosol Dry Powder Formulations

It is also contemplated that the present pharmaceutical formulation will be used as a dry powder inhaler formulation comprising a finely divided powder form of the complement inhibitory protein and a dispersant. The form of the complement inhibitory protein will generally be a lyophilized powder. Lyophilized forms of complement inhibitory proteins can be obtained through standard techniques.

In another embodiment, the dry powder formulation will comprise a finely divided dry powder containing one or more complement inhibitory proteins, a dispersing agent and also a bulking agent. Bulking agents useful in conjunction with the present formulation include such agents as lactose, sorbitol, sucrose, or mannitol, in amounts that facilitate the dispersal of the powder from the device.

Pulmonary Therapy with Complement Inhibitory Proteins

The complement inhibitory proteins of the invention are useful in the prophylactic or therapeutic treatment of complement mediated or complement related diseases or disorders in which pulmonary administration is desirable or in which the lungs are involved. The invention contemplates pulmonary administration of such amounts of the protein that are sufficient either to achieve systemic delivery of a complement inhibitory amount of the protein, or such amounts that achieve only local delivery of a complement inhibitory amount of the protein to the lung. The invention further contemplates parenteral administration or pulmonary administration of a complement inhibitory protein for the treatment of bronchoconstriction or for the treatment of anaphylaxis (including bronchoconstriction associated with anaphylaxis). It will be appreciated by one skilled in the art that goal of systemic or local delivery will depend on the indication being treated.

What constitutes a therapeutically effective amount in a particular case will depend on a variety of factors within the knowledge of the skilled practitioner. Such factors include the physical condition of the subject being treated, the severity of the condition being treated, the disorder or disease being treated, and so forth. In general, any statistically significant attenuation of one or more symptoms associated with inappropriate complement activity constitutes treatment within the scope of the present invention. Based on the results with animals described below, it is anticipated that for most mammals, including humans the administered dose for pulmonary delivery will be about 0.01 mg/kg to 100 mg/kg.

It is contemplated that complement inhibitory proteins, or more preferably the formulations of the present invention, can be administered to a subject in need of prophylactic or therapeutic treatment. As used herein, the term "subject" refers to an animal, more preferably a mammal, and most preferably a human.

Pulmonary Administration of a Complement Inhibitory Protein for Systemic Effects It is envisioned that the complement inhibitory proteins will be delivered to achieve elevation of plasma levels of the protein to treat diseases or disorders that involve inappropriate complement activity, i.e., extrapulmonary indications. Diseases or disorders involving complement that require systemic or circulating levels of complement regulatory proteins are detailed in Section 2.2 supra and in Table I that follows.

TABLE I

| Systemic Diseases and Disorders Involving Complement |
|---|
| Neurological Disorders |
| multiple sclerosis |
| stroke |
| Guillain Barre Syndrome |
| traumatic brain injury |
| Parkinson's Disease |
| Disorders of Inappropriate or Undesirable complement Activation |
| hemodialysis complications |
| hyperacute allograft rejection |
| xenograft rejection |
| interleukin-2 induced toxicity during IL-2 therapy |
| Inflammatory Disorders |
| inflammation of autoimmune diseases |
| Crohn's disease |
| adult respiratory distress syndrome |
| thermal injury including burns or frostbite |
| Post-Ischemic Reperfusion Conditions |
| myocardial infarction |
| balloon angioplasty |
| post-pump syndrome in cardiopulmonary bypass or renal bypass |
| hemodialysis |
| renal ischemia |
| mesenteric artery reperfusion after acrtic reconstruction |
| Infectious Disease or Sepsis |
| Immune Complex Disorders and Autoimmune Diseases |
| rheumatoid arthritis |
| systemic lupus erythematosus (SLE) |
| SLE nephritis |
| proliferative nephritis |
| glomerulonephritis |
| hemolytic anemia |
| myasthenia gravis |

In particular, those disorders with may be treated by the present route of administration are described in section 2.2 supra. In specific embodiments, disorders associated with extended zones of tissue destruction due to burn or myocardial infarct-induced trauma, and adult respiratory distress syndrome (ARDS), also known as shock syndrome, can be treated by pulmonary administration of an effective amount of a complement inhibitory protein.

An effective amount of soluble CR1 according to a preferred embodiment of the present invention for treatment of the disease of disorder is in the dose range of 0.01–100 mg/kg; preferably 0.1–10 mg/kg. As used herein, an effective amount of a complement inhibitory protein for treatment of a disease or disorder involving complement is an amount effective to inhibit complement activity systemically. An amount administered via the pulmonary route to achieve such circulating levels of soluble CR1 is envisioned. The dose may be administered in a single dosage via inhalation of the protein or in multiple doses.

Pulmonary Administration of a Complement Inhibitory Protein for Local Effects

In another embodiment of the present invention the complement inhibitory protein is delivered via the airways to treat diseases or disorders involving complement when such diseases or disorders are manifest by local injury to the lung. Such complement related diseases and disorders are listed in Table II.

TABLE II

Lung Disease and Disorders Involving Complement

Diseases dyspnea
hemoptysis
ARDS
asthma
chronic obstructive pulmonary disease (COPD)
emphysema
pulmonary embolisms and infarcts
Pneumonia infectious
aspiration
Fibrogenic dust diseases inert dusts and minerals including but not
limited to: silicon, coal dust, beryllium, and
asbestos
Pulmonary fibrosis
Organic dust diseases
Chemical injury (e.g., Irritant gasses and chemicals)

chlorine
phosgene
sulfur dioxide
hydrogen sulfide
nitrogen dioxide
ammonia
hydrochloric acid
Smoke injury
Thermal injury burn
freeze
Asthma allergy
bronchoconstriction
other causes of asthma, e.g., irritants
Others hypersensitivity pneumonitis
parasitic disease
Goodpasture's Syndrome
pulmonary vasculitis
immune complex-associated inflammation As pointed out above, pulmonary administration of a complement inhibitory protein is preferred for the treatment of lung disorders or diseases because of the high local concentration of complement inhibitory protein that can be delivered, the localization of significant amounts of the complement inhibitory protein in extravascular space, and the ability to limit or minimize systemic effects of the complement inhibitory protein.

It is particularly contemplated that a formulation of the present invention can be used for prophylaxis or therapy of smoke inhalation injury.

Use of Complement Inhibitory Proteins for the Treatment of Bronchoconstriction

As demonstrated in an example infra, complement inhibitory proteins of the invention can be used for the treatement of bronchoconstriction. The complement inhibitory protein can be administered systemically, and more preferably parenterally, i.e., via an intraperitoneal, intravenous, perioral, subcutaneous, intramuscular, intraarterial, etc. route, in order to treat bronchoconstriction. In a preferred embodiment, the complement inhibitory protein can be administered via the pulmonary route in order to treat bronchoconstriction. Pulmonary administration of a complement inhibitory protein is described above.

Bronchoconstriction can result from a number of conditions or disorders. These include but are not limited to asthma, especially allergic asthma, anaphylaxis, especially immune-mediated anaphylaxis, chronic obstructive pulmonary disease, and various non-specific irritants or lung insults, such as are included Table II, supra, under the headings "Diseases," "Chemical Injury," "Smoke Injury," "Organic Dust Diseases," "Fibrogenic Dust Diseases," "Smoke Injury" and "Thermal Injury." It is particularly contemplated that the systemic or pulmonary administration of a complement inhibitory protein can be used for prophylactic or therapeutic treatment of bronchoconstriction resulting from smoke inhalation.

Use of Complement Inhibitory Proteins for the Treatment of Anaphylaxis

In a specific embodiment, a complement inhibitory protein can be used in the treatment of anaphylaxis, in particularly hyperimmune anaphylaxis. Anaphylaxis is a systemic immune response caused by exposure to a substance to which a subject has become hypersensitive. Such reactions are unexpected, and can be life threatening. Anaphylaxis usually occurs within minutes to hours of exposure to the antigen. Many proteins and polypeptides can produce anaphylaxis in a subject (See, e.g., Lichtenstein and Fauci, *Current Therapy in Allergy and Immunology*, B. C. Decker Inc.: Philadelphia, esp. p. 79).

In another aspect of the invention, a complement inhibitory protein can be administered prophylactically or therapeutically for the treatment of an anaphylactoid reaction or idiopathic anaphylaxis. Anaphylactoid reactions or idiopathic anaphylaxis involve nonimmunologic release of the same or similar agents as in anaphylaxis. Such reactions usually are caused by exposure to various therapeutic or diagnostic agents, such as contrast media used in radiologic examinations. Some agents known to cause anaphylactoid reactions include but are not limited to acetyl salicylic acid, non-steroidal anti-inflammatory agents, curare, narcotics, mannitol and iodinated radiopaque contrast agents.

For the prophylaxis or treatment of anaphylaxis, or anaphylactoid reactions or idiopathic anaphylaxis, the complement inhibitory protein can be administered systemically, and more preferably parenterally, i.e., via an intraperitoneal, intravenous, perioral, subcutaneous, intramuscular, intraarterial, etc. route, in order to treat anaphylaxis. In a preferred embodiment, the complement inhibitory protein can be administered via the pulmonary route in order to treat anaphylaxis, especially for the treatment of bronchoconstriction associated with anaphylaxis. In addition to bronchoconstriction, administration of a complement inhibitory protein can attenuate or prevent blood pressure changes, decrease in circulating platelet count, and shock associated with anaphylaxis. Pulmonary administration of a complement inhibitory protein is described above.

In a specific example infra, soluble CR1 reduces or eliminates symptoms of anaphylaxis resulting from antigen challenge of a passively or actively immunized subject. In a specific embodiment, the sCR1 is administered by i.p. and/or i.v. route.

Animal Models for Evaluating the Formulations of the Invention

In a preferred aspect of the invention, the complement inhibitory protein or formulation of the invention is effective in inhibiting complement activity associated with anaphylaxis in the following model system. Guinea pigs are actively sensitized with ovalbumin in complete Freund's adjuvant (see Example 6, infra). Two groups of about seven or so animals are used. Group 1 is a control group which receives phosphate buffered saline. Group 2 is treated with a complement inhibitory protein, e.g., soluble CR1. At −1 hour, the animals are anesthetized, e.g., with pentobarbital or possibly ketamine/xylazine, and instrumented for measurement of bronchoconstriction and blood pressure. At −7 min, arterial blood samples are obtained. Samples of about 0.5 ml are appropriate. At −5 min the PBS or complement inhibitory protein (in a solution with a dispersant, e.g., a surfactant such as Tween 20), in particular sCR1, is aerosolized and administered by inhalation for about 3 min in about 3 ml volume. Aerosolization can be accomplished with a nebulizer, such as a DeVilbiss Porta Sonic Nebulizer. The compliance and resistance recorders for measuring bronchoconstriction and blood pressure should be interrupted during pulmonary administration of the aerosol formulation. At −2 min, the recording of compliance and resistance are resume. A blood sample is obtained at −1 min. At time 0, ovalbumin is administered parenterally or, more preferably, by inhalation. For example, a 1% ovalbumin solution in Tween 20 can be nebulized for 12 sec through the pneumotachograph and pump using a DeVilbiss Model 65 Ultrasonic Nebulizer. The amount of ovalbumin (or its concentration) can be varied up or down to induce a satisfactory response. Blood samples are obtained at +2, +7 and +20 min, and compliance and resistance measured continuously. After completion of the experiment, bronchoalveolar lavage (BAL) will be collected (about 15 ml) and BAL cells will be counted. The BAL supernatant will be tested to determine complement inhibitory protein, e.g., sCR1 levels and for protein content. Blood samples are used for counts of circulating white cells and platelets. Differential blood counts can be done and hematocrit obtained. Plasma samples can be tested to determine the level of C3 conversion (a measure of complement activation) and the level of complement inhibitory protein, e.g., sCR1.

In another embodiment, the effectiveness of complement inhibitory proteins and the formulations of the invention for the treatment of smoke inhalation injury can be tested. Many models for smoke inhalation injury are known in the art. For example, smoke can be generated by thermolysis of a fuel, e.g., polytetrafluoroethylene, in a crucible furnace at a constant temperature of 600° C. with a constant airflow rate. The smoke can be mixed with oxygen and animals, e.g., rats, can be exposed to the smoke for an appropriate period of time, e.g., 20 min. Group comparisons can be made between those animals treated prophylactically or after exposure to the smoke with an effective dose of a complement inhibitory protein, such as sCR1. The sCR1 can be administered parenterally, such as is described in the example, infra, or by pulmonary administration.

The invention can be better understood by referring to the following example, which is provided merely by way of exemplification and is not intended to limit the invention.

Example: Complement Receptor 1 (CR1) Decreases Bronchoconstriction in a sensitized Guinea Pig Along with life threatening bronchoconstriction, systemic anaphylaxis involves a serious hypotensive response often complicated by cardiac arrhythmias. Products of complement system activation are potential mediators of systemic anaphylaxis. The present example shows that the soluble complement receptor 1 (sCR1) can be used to inhibit activation of the classical and alternative pathways of complement in the guinea pig and will prevent bronchoconstriction and changes in blood pressure induced by intravenous antigen injection in guinea pigs either passively or actively sensitized to the antigen ovalbumin.

6.1. Materials and Methods

Respiratory and Blood Pressure Measurements

Pulmonary resistance and dynamic lung compliance were measured continuously in mechanically respirated, pentobarbital-anesthetized (25 mg/kg, i.p.) male guinea pigs (Hartley guinea pigs, Harlan Sprague-Dawley, Inc., Indianapolis, Ind. or Sasco, Inc., Omaha, Nebr.) as described previously (Regal and Bell, 1987, Int. Archs. Allergy Appl. Immun. 84:414–423). Tracheal airflow was measured with a Fleisch pneumotachograph and transpulmonary pressure measured via a needle inserted in the pleural cavity. Both tracheal airflow and transpulmonary pressure were fed into an on-line pulmonary mechanics computer (Model 6, Buxco Electronics, Sharon Conn.) which calculated pulmonary resistance and dynamic lung compliance by the method of Amdur and Mead (1958, Am. J. Physiol. 192:364–370). Mean arterial blood pressure was monitored via the femoral artery using a Statham PM23Db pressure transducer. A jugular vein was cannulated for administration of drugs and a carotid artery for blood sampling. Animals were allowed to stabilize 15 to 20 min prior to experimental manipulations. Because of tachyphylaxis, each animal received only one dose of antigen. Results are expressed as the mean±S.E. of the percentage of change from the control compliance, resistance or blood pressure before ovalbumin (OA) or bovine serum albumin (BSA) addition. After injection of OA or BSA, data were collected for 20 min. The average response in percent change for each group of animals at each 6-second interval is plotted. For clarity, standard error bars are included only at selected time points. For studies assessing the effect of sCR1 on the responsiveness to histamine or bradykinin, increasing doses of the agonist were given at 1-min intervals and the maximum percent change for each dose was determined.

Active and Passive Sensitization

Guinea pigs (200–300 g) were actively sensitized by the i.p. injection on days 0,2, and 4 of 0.4 ml of an emulsion made by mixing equal volumes of complete Freund's adjuvant with ovalbumin (5 mg/ml) in normal saline solution (NSS). Actively sensitized guinea pigs were challenged with antigen intravenously on days 21–34, at which time they had attained a weight of 350–450 g.

For passive sensitization, IgG antibody to ovalbumin was obtained from pooled serum samples of guinea pigs immunized with ovalbumin, and IgG and IgE-type antibodies to ovalbumin were separated by passage over a protein A-Sepharose column as previously described (Regal, 1984, J. Pharmacol. Exp. Ther. 228:116–120). Briefly, sera containing both IgG and IgE antibody to ovalbumin were passed over a protein A-Sepharose column. The antibody, plus other serum components that passed through the column, was characterized as IgE-type antibody by its heat lability in passive cutaneous anaphylaxis and its persistence in guinea pig skin for at least 14 days. The cytophilic antibody which was bound to the column was characterized as IgG by its heat stability in passive cutaneous anaphylaxis and its lack of persistence in guinea pig skin. The IgG fraction was a combination of $IgG_1$ and $IgG_2$ (Regal, 1984, supra).

IgG antibody was dialyzed against saline and stored in aliquots at −70° C. for later use. Passive sensitization of the guinea pigs was achieved by intracardiac injection of 1.6 mg/kg IgG under ether anesthesia 12–24 hrs before the experiment in guinea pigs weighing 225–300 g.

Measurement of C3 Conversion

C3 conversion was assessed using immunofixation techniques as described by Strong and Watkins (1979, J. Immunol. Methods 29:293–297). Plasma samples (1 ul) were applied to precut loading slits on Agarose Universal Electrophoresis film (Corning Medical, Palo Alto, Calif., USA) and electrophoresed for 90 min at 30 mA per film using Corning Universal barbital buffer containing EDTA. After electrophoresis, the film was overlaid with cellulose acetate strips soaked in the IgG fraction of goat anti-guinea pig C3 (Cooper Biomedical, East Chester, Pa., USA) and incubated at room temperature for 1 h. The film was then washed in normal saline solution, pressed, dried, and stained with Coomassie blue. A sample of yeast activated complement (YAC) was included on each gel to serve as a positive control, i.e., a sample with known C3 conversion. YAC was prepared as follows: Baker's yeast was first heat inactivated by boiling at 250 mg/ml in NSS for 30 min, and then incubated at 25 mg/ml with normal guinea pig serum at 37° C. for 60 min. The yeast was removed by centrifugation at 12,000 x g for 45 min and the supernatant (YAC) aliquoted and stored at −70° C.

Determination of sCR1 Plasma Levels

Concentrations of sCR1 in plasma samples were quantitated by a double polyclonal bead enzyme immunoassay as previously described (Mulligan et al, 1992, J. Immunol. 148:1479–1485).

Quantification of Peripheral Blood Cells

Arterial blood samples were collected into ethylenediamine tetra-acetic acid (EDTA) coated tubes. Total white blood cells and platelets were counted using a hemocytometer by standard procedures.

Materials

Histamine dihydrochloride, ovalbumin (Grade V), bovine serum albumin (Fraction V) and the acetate salt of bradykinin were obtained from Sigma Chemical (St. Louis, Mo.) Soluble complement receptor 1 (sCR1) containing LHRs A, B, C and D and SCRs 29 and 30, but lacking the transmembrane and cytoplasmic domains, has been described supra (Section 5.1). The sCR1 was prepared at a concentration of 5.96 or 5.08 mg/ml in phosphate buffered saline (PBS). sCR1 was prepared as previously described (Weisman et al, 1990, Science 249:146–151) using recombinant techniques, and contained less than 0.24 endotoxin units/ml as determined by the Limulus assay.

Experimental Design and Statistical Analysis

Four different experimental groups were addressed in this study: 1) passively sensitized guinea pigs receiving sCR1 at a dose of 15 mg/kg i.v. 2 min before challenge with 176 µg/kg ovalbumin; 2) actively sensitized guinea pigs receiving sCR1 at a dose of 15 mg/kg i.v. 2 min before challenge with 300 µg/kg ovalbumin; 3) actively sensitized guinea pigs receiving a cumulative dose of 105 mg/kg sCR1 i.p. and i.v. before challenge with 2 mg/kg of ovalbumin; and 4) actively sensitized guinea pigs receiving a cumulative does of 105 mg/kg sCR1 i.p. and i.v. before challenge with 2 mg/kg bovine serum albumin (BSA). The dosing regimen for animals receiving a cumulative dose of 105 mg/kg sCR1 was as follows: 24 hours prior to antigen or BSA challenge, 60 mg/kg sCR1 or 10.1 ml/kg PBS intraperitoneally; 5 minutes prior to antigen, 20 mg/kg sCR1 or 3.3 ml/kg PBS intravenously. In all 4 experimental groups, arterial blood samples were taken 1 or 2 min before i.v. administration of sCR1 or PBS, as well as 1 min before challenge with antigen or BSA. Either 2 or 3 arterial blood samples were also taken after antigen challenge for the assessment of C3 conversion, sCR1 plasma concentrations, and quantification of peripheral blood cells.

For determining differences in the time course of the percent change in compliance, resistance or blood pressure, the two tailed t test employed is Satterthwaites' approximation (Snedecor and Cochran, *Statistical Methods,* ed. 7, Iowa State University Press: Ames, Iowa, 1980) which does not assume equal variances. Repeated-measures analysis of variance was employed to determine if sCR1 affected the response to histamine or bradykinin as well as to determine if plasma levels of sCR1 were different in OA versus BSA challenged guinea pigs. To determine if sCR1 significantly affected the OA-induced changes in circulating cells, a two-tailed paired Student's t test was employed using log transformed values to stabilize variances. All tests used $p=0.05$ as the level of significance.

6.2 Results

Effect of 15 mg/kg sCR1 on the Response to OA in Active and Passive Sensitization The effect of a single intravenous injection of sCR1 (15 mg/kg) 2 min prior to OA challenge in both actively and passively sensitized guinea pigs was assesed (FIG. 1). OA challenge of passively sensitized guinea pigs (Experimental Group 1) resulted in a large increase in resistance and a large decrease in compliance. A transient hypertensive phase was followed by a precipitous drop in blood pressure. By 20 min blood samples could only be obtained by cardiac puncture. The administration of 15 mg/kg sCR1 did not significantly affect the response to antigen in passively sensitized guinea pigs.

A larger dose of ovalbumin was used in actively sensitized guinea pigs (Experimental Group 2) to insure that the compliance and resistance changes were as large as that seen with the passively sensitized guinea pigs. OA challenge of the actively sensitized guinea pig resulted in a bronchoconstriction similar in magnitude to that seen in the passively sensitized guinea pig. However, the blood pressure response was not as dramatic. The transient hypertensive phase was followed by only a moderate decrease in blood pressure. Treatment with 15 mg/kg sCR1 i.v. in the actively sensitized guinea pigs resulted in a very minor reduction in the OA-induced decrease in compliance, a marked shortening of the hypertensive phase of the blood pressure response and no hypotensive response. Soluble CR1 treatment did not significantly alter the baseline compliance, resistance or blood pressure compared to the PBS treated animals.

OA challenge of a passively sensitized guinea pig results in a precipitous drop in circulating white blood cells with minimal changes in circulating platelets accompanying the dramatic cardiovascular/pulmonary changes (FIG. 2). Soluble CR1 treatment did not alter the OA-induced changes in circulating cells in passively sensitized animals. In the actively sensitized guinea pig, OA-challenge was accompanied by a dramatic decrease in both circulating white blood cells and platelets. Soluble CR1 treatment significantly attenuated the OA-induced decrease in circulating platelets in the actively sensitized guinea pig, suggesting that this reduction in circulating platelets was dependent on complement activation. Soluble CR1 treatment did not significantly affect the baseline numbers of circulating white blood cells or platelets as determined by comparing cell counts before sCR1 treatment (−5 min) to those immediately before OA challenge (−1 min).

Figure 3B:
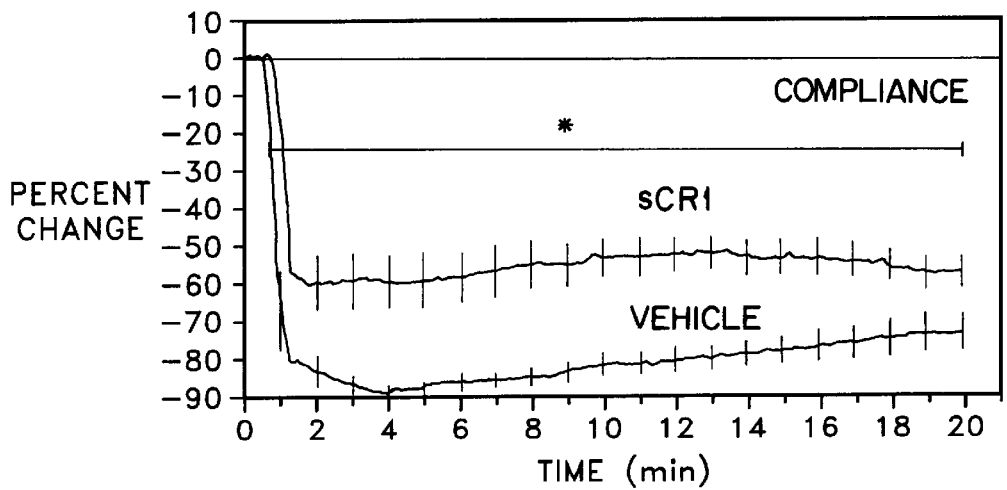
Figure 3C:
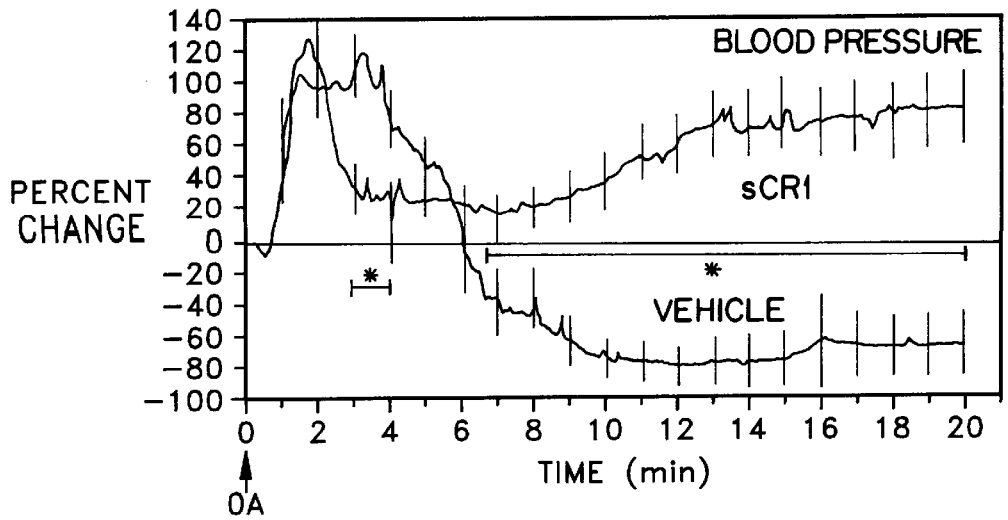

Effect a Cumulative sCR1 on the Response to OA, BSA, Histamine, and Brandykinin in Actively Sensitized Guinea Pigs Since our initial experiments with actively sensitized guinea pigs had demonstrated that sCR1 treatment shortened the hypertensive response to OA challenge, our continued experiments employed a higher dose of sCR1 administered over a 24 hour period prior to OA challenge. Preliminary studies in the rat had suggested that multiple dosing of sCR1 at higher doses would result in extravascular distribution of the molecule. Thus the response to OA challenge was assessed in actively sensitized guinea pigs, which had received a cumulative dose of 105 mg/kg sCR1 i.p. and i.v. over a 24 hour period prior to OA challenge (Experimental Group 3). These actively sensitized guinea pigs were challenged with a higher dose of OA to insure that a large hypotensive response to antigen would also occur. As seen in FIG. 3, sCR1 significantly inhibited the OA-induced decrease in compliance and increase in resistance. The hypertensive response to OA was shortened and the hypotensive response eliminated. Additionally, OA challenge was lethal in 5 of the 9 PBS treated animals, whereas all 9 of the sCR1 treated animals survived the 20 min course of the experiment.

Figure 4:
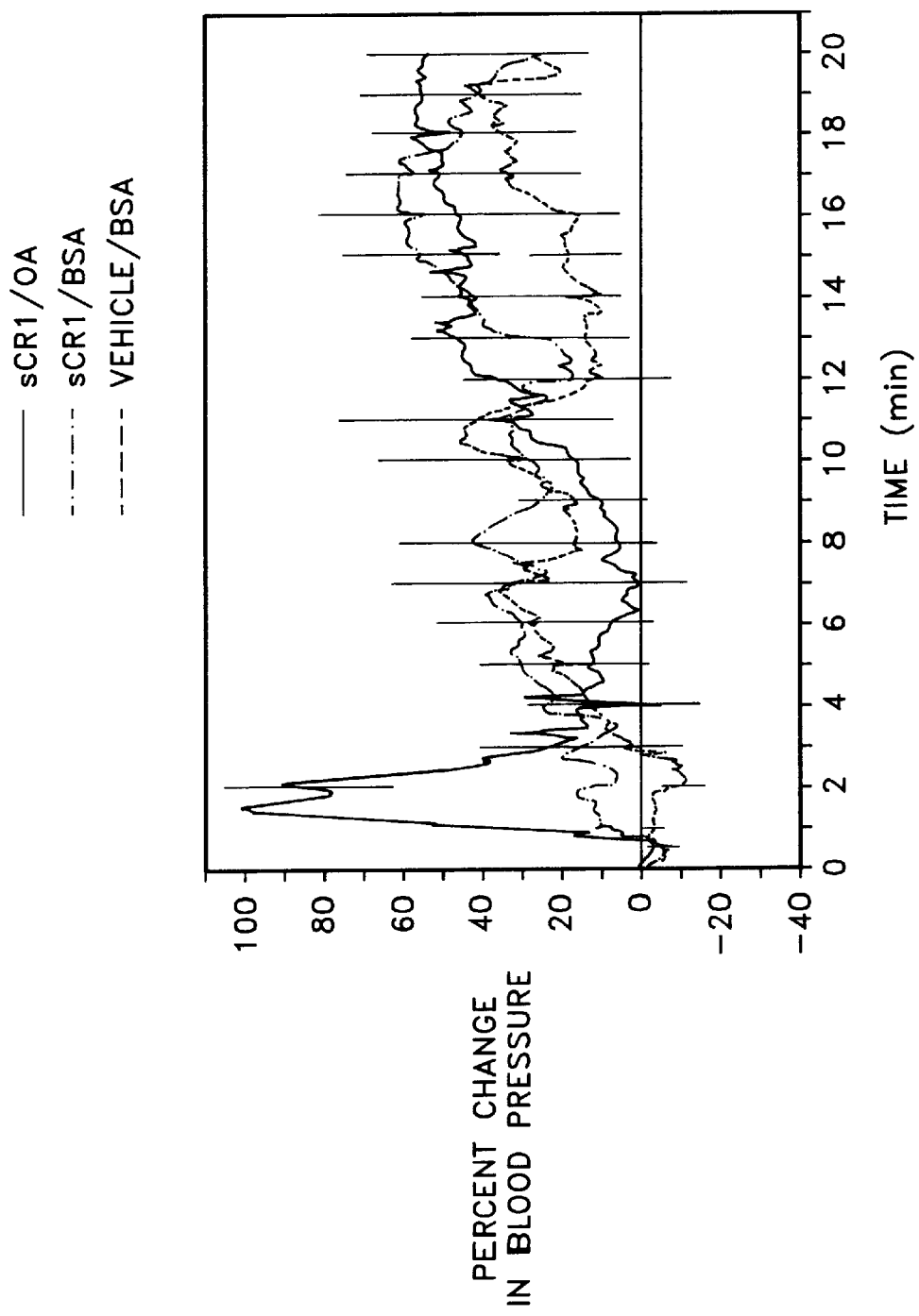
FIG. 4. Effect of sCR1 and PBS (vehicle) on the change in blood pressure in actively sensitized, guinea pigs. Ovalbumin or bovine serum albumin was administered i.v. at time 0 at a dose of 2 mg/kg. A cumulative dose of 105 mg/kg sCR1 or PBS (vehicle) was administered to guinea pigs challenged with either ovalbumin or bovine serum albumin (Experimental Groups 3 and 4, respectively). Values represent the mean ±S.E. of data from 4 to 9 different animals.

A group of actively sensitized guinea pigs pretreated with either PBS or sCR1 received BSA challenge as a control (Experimental Group 4). Soluble CR1 administered intravenously at −5 min in Experimental Group 3 and 4 did not significantly alter the baseline compliance, resistance, blood pressure, circulating white blood cells or platelets when compared to changes occurring in the PBS treated controls. Initial values of compliance, resistance, blood pressure, circulating white blood cells, and platelets at the time of OA or BSA addition were also not different. After BSA challenge, compliance and resistance changes were minimal, with less than a ±5% fluctuation from the baseline over the 27 min time period monitored after PBS or sCR1 administration i.v. (data not shown). Fluctuations in blood pressure in BSA challenged animals were more pronounced (FIG. 4). Actively sensitized guinea pigs treated with a cumulative dose of 105 mg/kg sCR1 or the control PBS injections and then challenged with BSA experienced an increase in blood pressure over the 20 min period monitored after BSA challenge. This slow rise in blood pressure is indistinguishable from that observed in sCR1 treated animals challenged with OA. The sCR1 treated animals challenged with OA also showed the transient hypertensive phase characteristic of the intravenous antigen challenge in the guinea pig. The slow rise in blood pressure also occurred in animals treated with PBS and challenged with BSA. Thus, this slow rise in blood pressure was not an effect of the sCR1 itself.

Figure 5A:
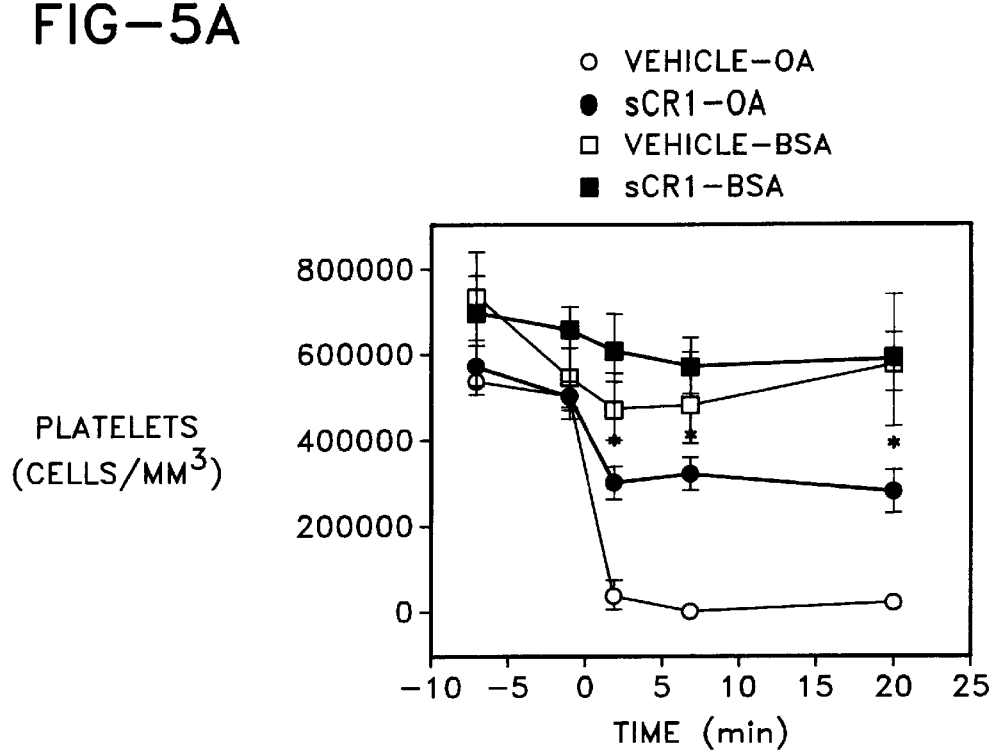
FIGS. 5A–B. Effect of sCR1 or PBS on ovalbumin or bovine serum albumin-induced changes in circulating platelets (A) or white blood cells (B). Ovalbumin or bovine serum albumin was administered i.v. at time 0 at a dose of 2 mg/kg. A cumulative dose of 105 mg/kg sCR1 or PBS was administered to guinea pigs challenged with either ovalbumin or bovine serum albumin (Experimental Groups 3 and 4, respectively). Values represent the mean ±S.E. of determinations in 4 to 9 different animals. An asterisk (*) represents a statistically significant difference (p<0.05) in the ovalbumin-induced change in circulating cells in sCR1 treated animals compared to PBS (vehicle) treated animals.
Figure 5B:
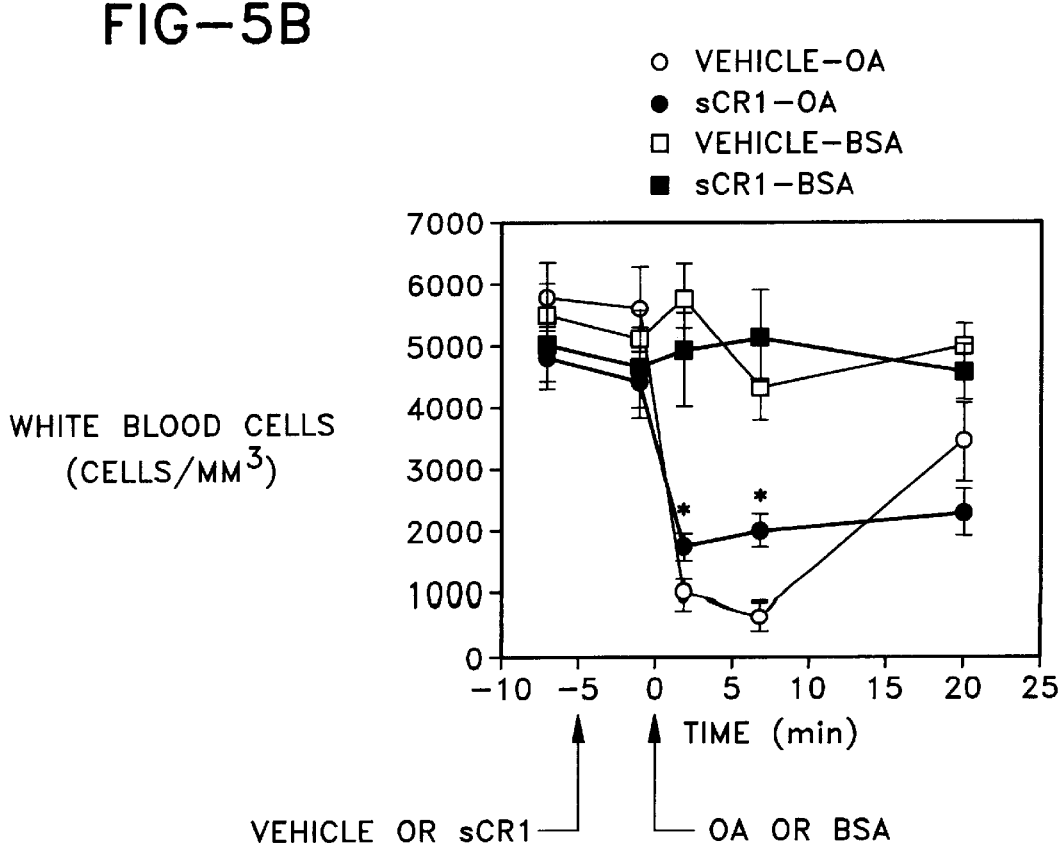

The effect of a cumulative dose of 105 mg/kg sCR1 on the OA and BSA-induced changed in circulating cells was also investigated (Experimental Groups 3 and 4). As seen in FIG. 5, BSA challenge of PBS or sCR1 treated animals showed minimal changes in circulating cell numbers. However, challenge of actively sensitized guinea pigs with 2 mg/kg OA resulted in a precipitous drop in both circulating white blood cells and platelets. Soluble CR1 treatment significantly inhibited the decrease in the circulating platelets at all time points after OA challenge and the decrease in WBC at 2 and 7 min after OA challenge. The higher dose of 105 mg/kg sCR1 did not inhibit the OA-induced decrease in platelets to a greater extent than 15 mg/kg sCR1 i.v. (FIG. 2).

Figure 7:
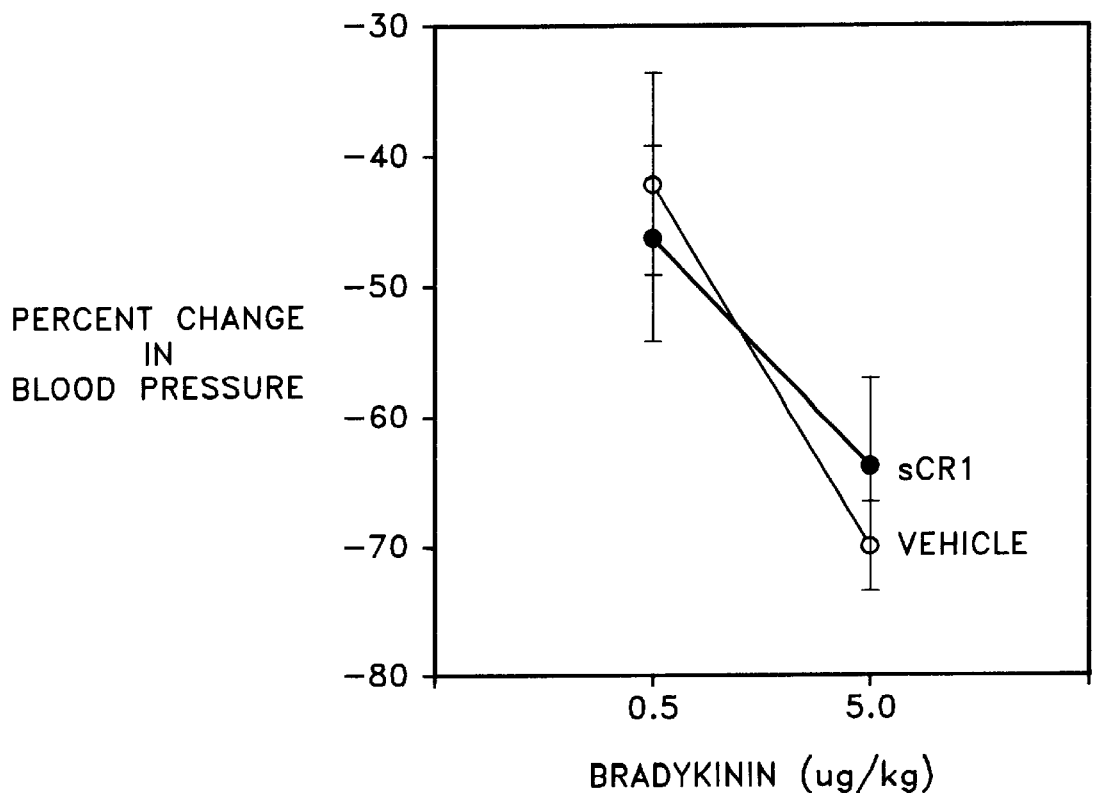
FIG. 7. Effect of a cumulative dose of 105 mg/kg sCR1 on the response of the guinea pig to bradykinin (Experimental Group 4). Values represent the mean ±S.E. of determinations in 4 animals, pretreated with either PBS (vehicle) or sCR1 prior to bovine serum albumin challenge and evaluation of the responsiveness to histamine followed by bradykinin.

In Experimental Group 4, after the response to BSA was monitored, guinea pigs were challenged with histamine, hyperinflated to return compliance and resistance to baseline values and then challenged with bradykinin. As seen in FIG. 6, the bronchoconstrictor response to histamine was not affected by sCR1 treatment. Histamine also caused a 20 to 30% decrease in blood pressure which was unaffected by sCR1 pretreatment (data not shown). The effect of sCR1 treatment on the response to bradykinin was also evaluated since bradykinin produces a more pronounced decrease in blood pressure compared to histamine. Soluble CR1 treatment did not significantly affect the decrease in blood pressure induced by two successive doses of bradykinin (FIG. 7). Bradykinin also caused a significant bronchoconstriction at these doses and the decrease in compliance and increase in resistance was not significantly affected by sCR1 (data not shown).

C3 Conversion

Figure 8:
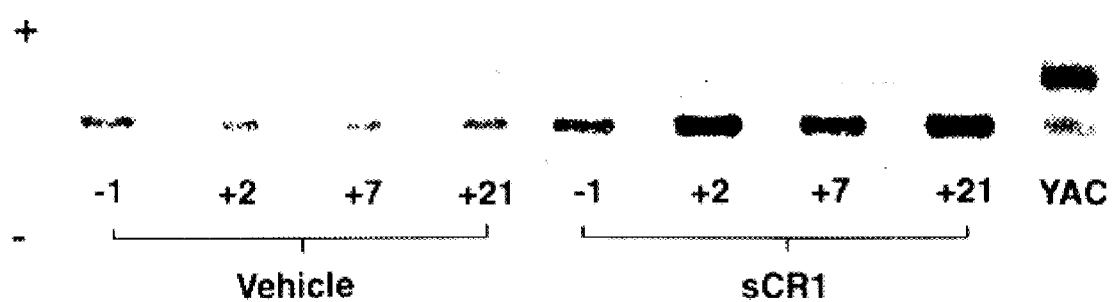
FIG. 8. Effect of a cumulative dose of 105 mg/kg sCR1 on C3 conversion in ovalbumin challenged guinea pigs. Data shown is from an sCR1 and PBS (vehicle) treated guinea pig in Experimental Group 3. Animals were challenged with ovalbumin (2 mg/kg) at time 0. Yeast activated complement (YAC) served as a positive control.

Soluble CR1 clearly inhibited the OA-induced bronchoconstriction and hypotension, suggesting that complement activation was an essential step in these events. To determine if complement system activation could be demonstrated after OA challenge, we assesed the presence or absence of detectable C3 conversion. In the process of complement activation, the complement component C3 is cleaved into C3a (9.1 kDA) and C3b (180 kDa) fragments by the enzyme C3 convertase. The cleavage product C3b is then further degraded by enzymatic action to fragments such as C3bi, C3c, and C3dg. If serum samples from an animal are electrophoresed to separate the intact C3 molecule from its cleavage products C3b, C3bi, etc., and then probed with an antibody to guinea pig C3, two major bands are revealed: the intact C3 molecule and a broader band consisting of various C3 cleavage products) (Strong and Watkins, 1979, J. Immunol. Methods 29:293–297). In this way, an estimate of 'C3 conversion' or cleavage of the C3 molecule indicating complement activation can be obtained. Results from one PBS and one sCR1 treated animal is shown in FIG. 8. Challenge of an actively sensitized guinea pig with 2 mg/kg OA (Experimental Group 3) resulted in detectable C3 conversion at all three time points examined in a PBS pretreated animal (2, 7, and 20 min after OA). Six of the 7 PBS treated animals examined had evidence of C3 conversion at all time points after OA challenge as compared to 0 of 7 sCR1 treated animals. No C3 conversion was detectable prior to OA challenge in either the PBS or sCR1 treated guinea pigs or after OA challenge in the sCR1 treated animals.

C3 conversion was also assessed in actively sensitized guinea pigs treated with 15 mg/kg sCR1 and challenged with 300 μg/kg OA (Experimental Group 2). In these animals, no C3 conversion could be detected 2 min after OA challenge but C3 conversion was clearly evident 20 min after OA challenge in all 5 PBS treated animals and in zero of 5 sCR1 treated animals. Thus, OA challenge of actively sensitized guinea pigs is accompanied by activation of the complement system as assessed by C3 conversion. No C3 conversion was detected at any time points in BSA challenged animals treated with either PBS or sCR1 (Experimental Group 4).

Plasma Concentrations of sCR1

In all experimental groups, animals pretreated with PBS had no detectable sCR1 in the plasma. Soluble CR1 levels of guinea pigs treated with 15 mg/kg i.v. sCR1 (Experimental Group 1 and 2) are shown in Table III. Comparable plasma concentrations of sCR1 were attained in both passively and actively sensitized guinea pigs. However, the hypertensive response was only affected in actively sensitized guinea pigs.

Figure 9:
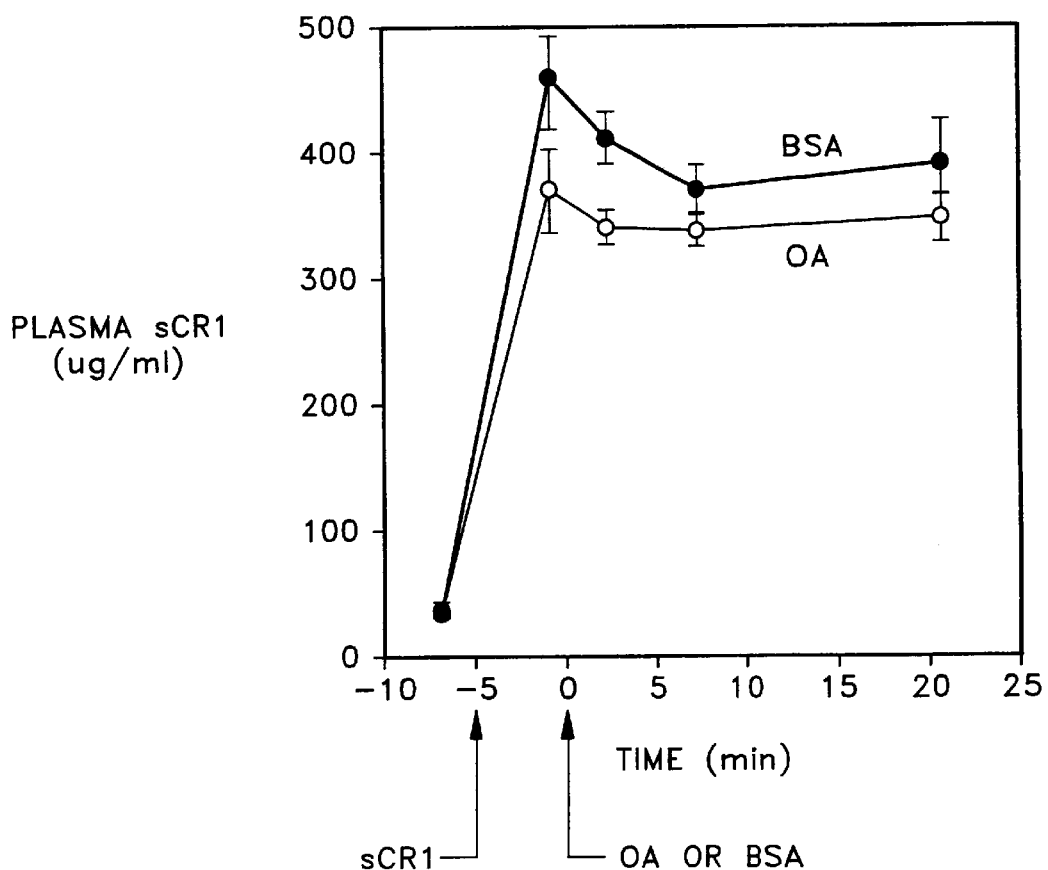
FIG. 9. Plasma levels of sCR1 in guinea pigs (Experimental Groups 3 and 4). Values represent the man ±S.E. of 7 or 4 determinations in ovalbumin or bovine serum albumin challenged animals, respectively. sCR1 was administered at −24 hr, −3 hr and −5 min and ovalbumin or bovine serum albumin at time 0.

Plasma concentrations of sCR1 in guinea pigs that received a cumulative dose of 105 mg/kg sCR1 are shown in FIG. 9. Soluble CR1 concentrations did not significantly differ as determined by repeated measured ANOVA in OA vs BSA challenged animals. Plasma concentrations of sCR1 were compared at 2 and 20 min after OA challenge in actively sensitized guinea pigs treated with either 15 mg/kg i.v. sCR1 (Experimental Group 2, Table III) or 105 mg/kg sCR1 (Experimental Group 3, FIG. 9). Plasma concentrations of sCR1 were significantly different at 20 min after OA challenge but not 2 min after OA challenge.

TABLE III

Plasma concentrations of sCR1 in actively and passively sensitized guinea pigs. 15 mg/kg sCR1 was administered i.v. at −2 min and guinea pigs were challenged with OA at time 0 (Experimental Groups 1 and 2). Values are the mean ± I S.E. of 4 to 5 experiments.

| Sensitization | Conc. of sCR1 ($\mu$g/ml) at time | | | |
|---|---|---|---|---|
| | −5 min | 2 min | 5 min | 20 min |
| Passive | N.D. | — | 254.2 ± 37.5 | 265.7 ± 29.4 |
| Active | N.D. | 354.4 ± 10.3 | — | 239.7 ± 22.2 |

N.D. = Not Detectable

Discussion

The results of this study clearly demonstrate the effectiveness of a complement inhibitory protein in reducing antigen-induced anaphylaxis. In particular, sCR1 has been shown to ameliorate or prevent many of the effects of anaphylaxis, including bronchoconstriction, blood pressure drop, and circulating platelet decrease. Furthermore, as explored more fully below, the present work is the first study to definitively implicate the complement system in anaphylaxis.

Anaphylaxis involved both serious respiratory and cardiovascular consequences. Along with life threatening bronchoconstriction, systemic anaphylaxis involves a serious hypotensive response. Knowledge of the sequence of events leading to the bronchoconstriction and hypotension is important in designing rational therapeutic regimens for the treatment of anaphylaxis. Our studies have demonstrated that inhibiting complement system activation using the molecule sCR1 will attenuate the bronchoconstrictor response as well as prevent the hypotension induced by antigen in an actively sensitized guinea pig model of anaphylaxis. These results indicate that complement system activation contributes to the bronchoconstrictor response and is essential for the hypotensive response. In addition, the studies have demonstrated that the anaphylactic response is accompanied by complement activation with a time course consistent with a role for complement system activation in the antigen-induced events.

The sCR1 molecule has been successfully used in the present Example to minimize the symptoms of anaphylaxis, and particularly, bronchoconstriction. Soluble CR1 prevents complement activation by reversibly binding to the C3b and C4b subunits of the C3 and C5 convertase enzyme complexes which are responsible for the cleavage of C3 and C5 and the continuation of the process of complement system activation. With binding, sCR1 displaces the catalytic subunits of the C3 and C5 convertases as well as causes the proteolytic inactivation of C3b and C4b by the plasma protease Factor 1.

Inhibition of symptoms of anaphylaxis by sCR1 provides evidence that complement activation is important in antigen-induced events. Activation of the complement system produces many biologically active products (Goldstein, 1992, supra) which could be involved, including opsonic fragments of C3, the anaphylatoxins (C3a, C4a, C5a), the leukocytosis promoting factor C3e, fragments of Factor B, and the Membrane Attack Complex C5b-9. The anaphylatoxins C3a/C5a are known to mimic the symptoms of anaphylaxis when injected into a guinea pig. Thus, they are potentially relevant products of complement system activation to mediate the antigen-induced bronchoconstriction and changes in blood pressure. However, another result of complement system activation, the Membrane Attack Complex, also stimulates metabolism of arachidonic acid (Morgan, 1989, Biochem. J. 264:1–14), a possible source of biologically active substances which could mediate the anaphylactic response.

These studies have shown that sCR1 does not alter the ability of the cardiovascular and respiratory systems to respond to histamine or bradykinin indicating it is not generally inhibiting cardiovascular and respiratory reactivity.

These studies have also demonstrated that C3 conversion occurred in the actively sensitized guinea pigs after antigen challenge. C3 conversion is a more sensitive indicator of complement activation than a measurement of total hemolytic complement activity, but is still far less sensitive than the measurement of C3a or C5a generation. Significant complement activation could be occurring even though C3 conversion is not detectable. Nonetheless, our studies have demonstrated the presence of C3 conversion as early as 2 min after antigen challenge when serious bronchoconstriction and blood pressure changes are occurring.

These studies have examined the role of complement system activation in two different models of guinea pig anaphylaxis. In one model (Experimental Group 1) the guinea pig was passively sensitized with a combination of IgG1 and IgG2 antibody to ovalbumin. In the other model, the guinea pigs were actively sensitized to ovalbumin using complete Freund's adjuvant. Studies of Richerson (1972, J. Lab. Clin. Med. 79:745–757) have demonstrated that sensitization with ovalbumin and complete Freund's adjuvant will result in the production of both IgG1 and IgG2 antibody to ovalbumin, whereas sensitization with low dose ovalbumin alone will result in the production of primarily IgG1 antibody to ovalbumin. Studies of Cheng, et al. (1987, Fed. Proc. 46:931) have indicated that active sensitization results in higher circulating concentrations of IgG than passive sensitization. This is predictable since the total amount of IgG antibody injected during passive sensitization in our studies represents the amount of IgG in less than 0.5 ml of serum from a hyperimmunized animal. The does of antigen required to generate a similar physiological response differed in the two models. Dose response curves were not generated because of tachyphylaxis, i.e. animals become unresponsive to antigen challenge after a single administration of antigen. Regardless of passive versus active sensitization, antigen challenge in either guinea pig model resulted in an intense bronchoconstriction and a transient hypertension followed by hypotension.

The effect of antigen on circulating cell populations also differed in the two different models of guinea pig anaphylaxis. In passively sensitized guinea pigs, antigen challenge did not result in significant changes in circulating platelets. Clearly, in this model, antigen-induced bronchoconstriction and changes in blood pressure occurred independently of an effect on circulating platelet numbers. In contrast, in the actively sensitized guinea pig, antigen challenge resulted in a decrease in the number of circulating platelets as well as white blood cells. Soluble CR1 treatment significantly shortened the antigen-induced hypertensive phase as well as antigen-induced decrease in circulating platelets. The dramatic effect on platelet changes indicated that sCR1 levels in the plasma were sufficient to have an effect at this site.

In the initial studies with a single i.v. treatment with sCR1, the antigen-induced response was slightly less than that in the PBS treated animals, though the effect was not significant. Thus, studies were initiated using higher doses of sCRI administered over a 24 hour period prior to antigen challenge. Similar plasma sCR1 levels were apparent at the time of antigen challenge whether animals were dosed with a single i.v. dose of 15 mg/kg or a cumulative does of 105 mg/kg. However, in the case of a cumulative dosing with 105 mg/kg, the antigen-induced decrease in compliance and increase in resistance was clearly inhibited and the hypotensive response to antigen was nonexistent. Our control studies also demonstrated that the cumulative dose of 105 mg/kg sCR1 did not inhibit the bronchoconstrictor response or drop in blood pressure induced by the exogenous administration of histamine or bradykinin. Thus, sCR1 was not acting nonspecifically to alter the cardiovascular/respiratory responses in the guinea pig at these doses. These studies also suggest that the important complement activation is occurring at extravascular sites. These extravascular sites are particularly attractive targets for direct pulmonary administration of sCR1, e.g., via inhalation.

These studies are the first to demonstrate convincing evidence that complement activation is an essential step in the antigen-induced bronchoconstriction and changes in blood pressure in an actively sensitized guinea pig model of anaphylaxis. Clearly, complement activation is occurring and interference with the activation attenuates the antigen-induced events. The study also reinforces the notion that the mechanism of anaphylaxis will vary significantly depending on the model system employed. Thus, continued studies of the differing mechanisms and mediators of anaphylaxis are of importance and the complement system clearly warrants consideration as a source of those mediators.

Example: Aerosol Administration of Soluble Complement Receptor 1 (sCR1) in Guinea Pig Models Mterials and Methods Guinea pigs (200–300 g) were actively sensitized by an i.p. injection of ovalbumin (1 mg) in Freund's adjuvant on days 0, 2, and 4. On day 21, sCR1 was administered to the sensitized guinea pigs by inhalation following nebulization (exposure to a nebulized 5 mg/ml solution of sCR1 or saline for 7–14 minutes via a tracheal tube). Thirty minutes after the beginning of sCR1 administration the guinea pigs were challenged by inhalation with nebulized OA (2.5% solution for 1 minutes). Pulmonary resistance, dynamic lung compliance and mean arterial blood pressure were measured continuously as described supra at section 6.1.1. Total WBC and platelets were counted in arterial blood samples. The sCR1 treatment showed an effect on resistance and blood pressure.

Respiratory and Blood Pressure Measurements

Pulmonary resistance, dynamic lung compliance and mean arterial blood pressure were measured continuously as described supra at section 6.1.1. Animals were allowed to stabilize 15 to 20 min prior to experimental manipulations. Results are expressed as the mean +/−S.E. of the percentage of change from the control compliance, resistance or blood pressure before ovalbumin (OA) addition. After inhalation OA, data were collected for 20 min.

Active Sensitization

Guinea pigs (200–300 g) were actively sensitized by the i.p. injection on days 0, 2, and 4 of 0.4 ml of an emulsion made by mixing equal volumes of complete Freund's adjuvant with ovalbumin (5 mg/ml) in normal saline solution (NSS). Actively sensitized guinea pigs were challenged with antigen by inhalation on Day 21. The guinea pigs inhaled a nebulized 2.5% solution of OA for 1 minute. The material was nebulized in an ultrasonic nebulizer (DeVillebiss Porta-Sonic, Somerset, Pa.).

Quantifications of Peripheral Blood Cells

Arterial blood samples were collected into ethylenediamine tetra-acetic acid (EDTA) coated tubes. Total white blood cells and platelets were counted using a hemocytometer by standard procedures.

Materials

Ovalbumin (Grade V) was obtained from Sigma Chemical (St. Louis, Mo.). Soluble complement receptor 1 (sCR1) containing LHRs A, B, C and D and SCRs 29 and 30, but lacking the transmembrane and cytoplasmic domains, has been described supra (Section 5.1). The sCR1 was prepared at a concentration of 5.08 mg/ml in phosphate buffered saline (PBS). sCR1 was prepared as previously described (Weisman et al., 1990, Science 249:146–151) using recombinant techniques, and contained less than 0.254 endotoxin units/ml as determined by the Limulus assay.

Experimental Design and Statistical Analysis

Two experimental groups were used in the study. One group received sCR1 by aerosol and the other received saline thirty minutes before OA challenge. The guinea pigs were exposed to a nebulized 5 mg/ml solution of sCR1 or sterile saline for 10 minutes.

In both experimental groups, arterial blood samples were taken before aerosol administration of sCR1 or PBS, as well as 1 min before challenge with OA. Either 2 or 3 arterial blood samples were also taken after antigen challenge for the quantification of peripheral blood cells.

For determining differences in the time course of the percent change in compliance, resistance or blood pressure, the two tailed t test employed is Satterthwaites' approximation (Snedecor and Cochran, *Statistical Methods,* ed. 7, Iowa State University Press: Ames, Iowa, 1980) which does not assume equal variances. To determine if sCR1 significantly affected the OA-induced changes in circulating cells, a two-tailed paired Student's t test was employed using log transformed values to stabilize variances. All Tests used p=0.05 as the level of significance.

Results

OA challenge of actively sensitized guinea pigs resulted in a large increase in resistance and a large decrease in compliance. A transient hypertensive phase was followed by a precipitous drop in blood pressure. The administration of sCR1 by aerosol lowered the increase in pulmonary resistance and it reduced the severity of the hypotensive phase. OA challenge by aerosol of actively sensitized guinea pigs results in a precipitous drop in circulating white blood cells and a decrease in circulating platelets. Aerosol sCR1 treatment did not alter the OA-induced changes in circulating cells or platelets.

Example: Tissue Localization of sCR1 Following Inhalation

The tissue localization of sCR1 was studied in guinea pigs following inhalation of a nebulized saline solution of sCR1 (5 mg/ml) for 7 minutes. Control animals inhaled nebulized saline. The sCR1 was visualized by immunohistochemistry using a rabbit polyclonal anti-sCR1 antibody on formalin fixed paraffin sections. The sCR1 was present throughout the lung space and was deposited on the surface of the trachea, bronchi, bronchioles, alveolar ducts and terminal alveoli.

Materials and Methods sCR1 Administration

Mechanically respirated, anesthetized (ketamine 30 mg/kg i.m. xylazine 2.5 mg/kg i.m.) male guinea pigs (Hartley guinea pigs, Harlan Sprague-Dawley, Inc., Indianapolis, Ind. or Sasco, Inc., Omaha Nebr.) were administered a nebulized saline solution of sCR1 (5 mg/ml) for 7 minutes by inhalation. Control animals inhaled nebulized saline. The animals were euthanized and the lungs were preserved in formalin.

Immunoperoxidase Staining Procedures

Formalin fixed lung tissue was deparaffinized and rehydrated. The sections were stained for sCR1 using a rabbit anti-sCR1 antisera (T Cell Sciences, Inc., Cambridge, Mass.) and a VECTASTAIN Elite ABC kit (Vector Labs, Burlingame, Calif.). The primary antibody was used at a dilution of 1:300. The sections were counter stained by incubation in 1% (w/v) Methyl Green in methanol for 0.5–2 minutes.

Results

Figure 10A:
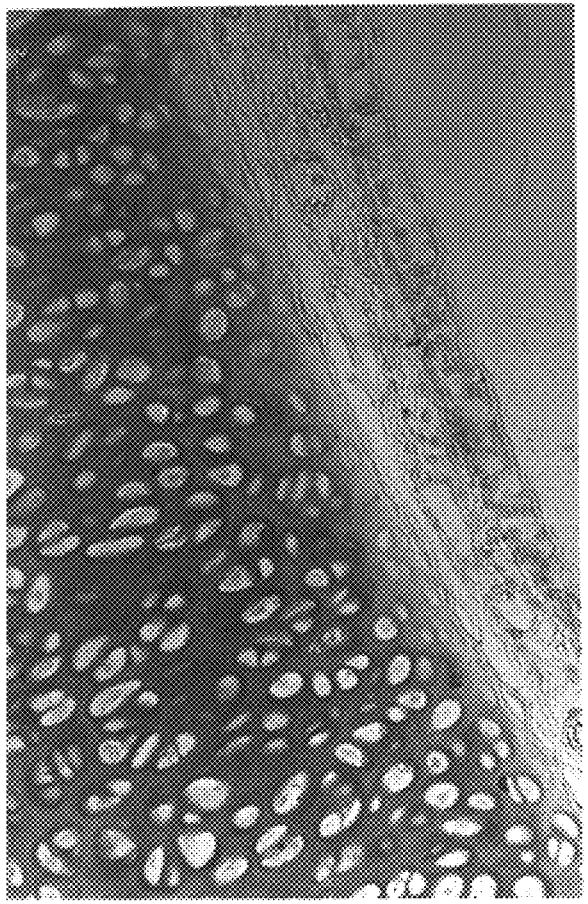
FIGS. 10A–B. Cross section of a guinea pig trachea from a control animal following inhalation of nebulized saline solution (10A), or an experimental animal following inhalation of a nebulized saline solution containing 5 mg/ml sCR1 (10B) for 7 minutes. sCR1 was visualized by immunohistochemical staining using a rabbit polyclonal anti-sCR1 antibody. sCR1 is localized in the tracheal mucosa following inhalation and appears as a black stain on a grey background.
Figure 10B:
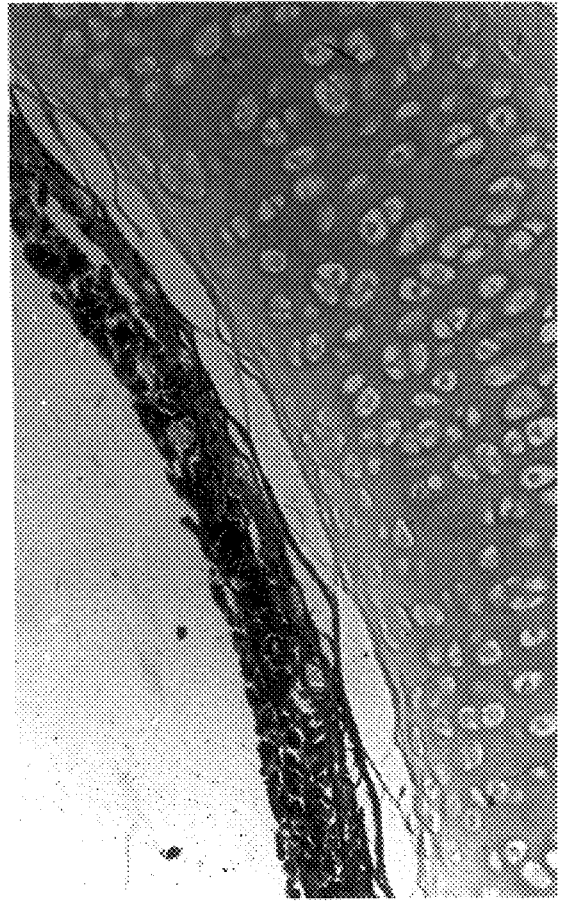

The sCR1 was present throughout the lung space and was deposited on the surface of the trachea, bronchi, bronchioles, alveolar ducts and terminal alveoli. In the figures the sCR1 stains black and the counterstained tissue appears gray. FIGS. 10 A and B show cross sections of a guinea pig trachea from a control animal following inhalation of nebulized saline solution (10 A), or an experimental animal following inhalation of a nebulized saline solution containing 5 mg/ml sCR1 (10 B) for 7 minutes. FIG. 10 demonstrates that sCR1 is localized in the tracheal mucosa following inhalation and appears as a black stain on a gray background.

Figure 11A:
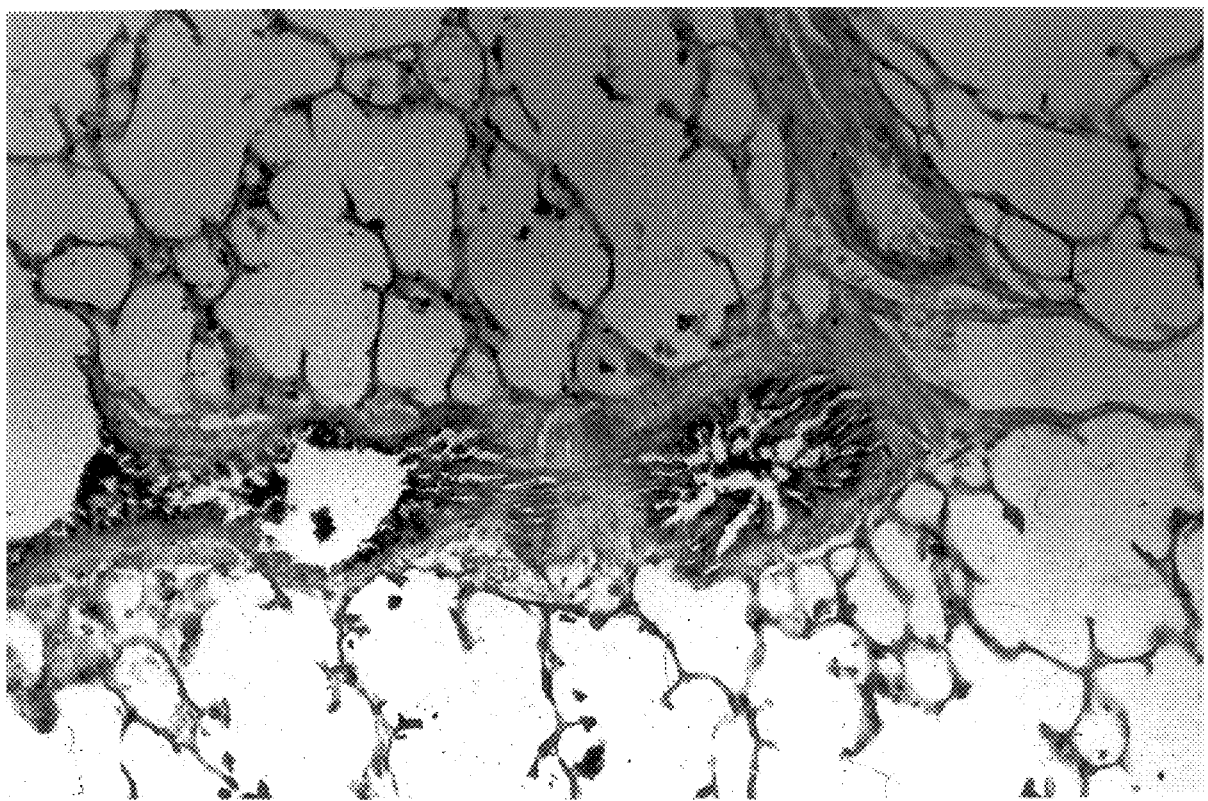
FIGS. 11A–B. Cross section of a guinea pig lung from a control animal following inhalation of nebulized saline solution (11A), or an experimental animal following inhalation of a nebulized saline solution containing 5 mg/ml sCR1 (11B) for 7 minutes. sCR1 was visualized by immunohistochemical staining using a rabbit polyclonal anti-sCR1 antibody. sCR1 appears as a black stain on a gray background. sCR1 was present in the lung and was deposited on bronchi and bronchioli, alveolar ducts and terminal alveoli.
Figure 11B:
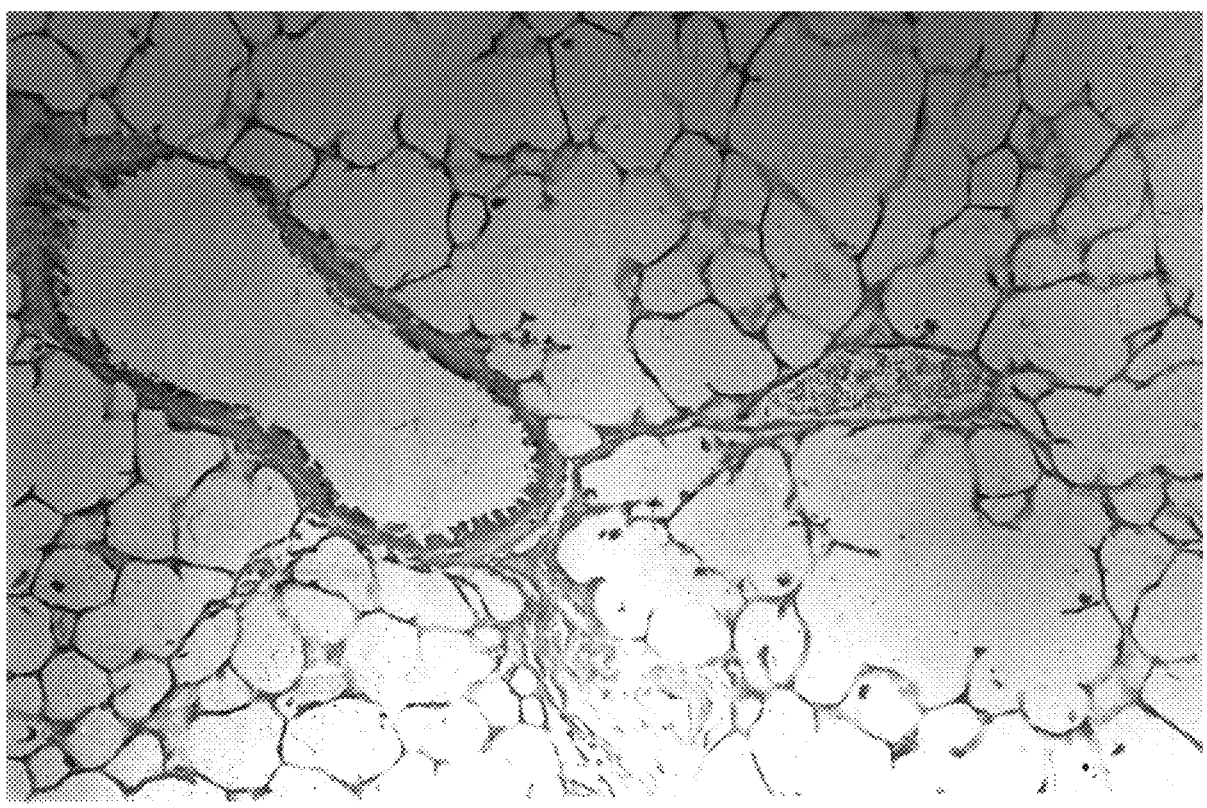

FIGS. 11 A and B show cross sections of a guinea pig lung from a control animal following inhalation of nebulized saline solution (11 A) or an experimental animal following inhalation of a nebulized saline solution containing 5 mg/ml sCR1 (11 B) for 7 minutes. sCR1 was visualized by immunohistochemical staining using a rabbit polyclonal anti-sCR1 antibody. In FIG. 11 B, sCR1 appears as a black stain on a gray background. sCR1 was present throughout the lung and was deposited on bronchi and bronchioli, alveolar ducts and terminal alveoli. FIG. 11 A shows no sCR1 in the same areas.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A method for administering a soluble complement receptor type 1 (sCR1) agent to a subject comprising;
   a) providing a sCR1 polypeptide or fragment, derivative, or analog thereof and a pharmaceutically acceptable dispersant in a formulation suitable for pulmonary delivery, wherein said sCR1 polypeptide or fragment, derivative, or analog thereof retains at least one complement-binding activity of an erythrocyte CR1 allotype; and
   b) administering said formulation to said subject via the pulmonary route.

2. The method according to claim 1 in which the dispersant is a surfactant.

3. The method according to claim 2 in which the surfactant is selected from the group consisting of polyoxyethylene fatty acid esters, polyoxyethylene fatty acid alcohols, and polyoxyethylene sorbitan fatty acid esters.

4. The method according to claim 3 in which the surfactant is polyoxyethylene sorbitan monooleate.

5. The method according to claim 2 in which the concentration of the surfactant is about 0.001% to about 4% by weight of the formulation.

6. The method according to claim 1 in which said formulation is a dry powder aerosol formulation in which the sCR1 polypeptide, fragment, derivative, or analog is present as a finely divided powder.

7. The method according to claim 6 in which the sCR1 polypeptide, fragment, derivative, or analog is lyophilized.

8. The method according to claim 6 wherein the formulation further comprises a bulking agent.

9. The method according to claim 8 in which the bulking agent is selected from the group consisting of lactose, sorbitol, sucrose and mannitol.

10. The method according to claim 1 in which said formulation is a liquid aerosol formulation comprising a pharmaceutically acceptable diluent.

11. The method according to claim 10 in which the diluent is selected from the group consisting of sterile water, saline, buffered saline and dextrose solution.

12. The method according to claim 11 in which the diluent is phosphate buffered saline in the pH 7.0 to 8.0 range.

13. A method for treating a disease or disorder involving complement comprising administering to a subject suffering from said disease or disorder, via the pulmonary route, a soluble complement receptor 1 (sCR1) polypeptide or fragment, derivative, or analog thereof in an amount effective to inhibit complement activity, wherein said sCR1 polypeptide or fragment, derivative or analog thereof retains at least one complement-binding activity of an erythrocyte CR1 allotype.

14. The method according to claim 13 in which the administered sCR1 is the same as that expressed by the Chinese Hamster Ovary cell DUX B11 carrying plasmid pBSCR1c/pTCSgpt as deposited with the ATCC and assigned accession number CRL 10052.

15. The method according to claim 13 in which the disease or disorder involving complement is selected from the group consisting of neurological disorders, disorders of inappropriate or undesirable complement activation, inflammatory disorders, post-ischemic reperfusion conditions, infectious disease, sepsis, immune complex disorders and autoimmune disease.

16. The method according to claim 13 in which the disease or disorder involving complement is a disorder of inappropriate or undesirable complement activation selected from the group consisting of hemodialysis complications, hyperacute allograft rejection, xenograft rejection and interleukin-2 induced toxicity during interleukin-2 therapy.

17. The method according to claim 13 in which the disease or disorder involving complement is a post-ischemic reperfusion condition selected from the group consisting of myocardial infarction, balloon angioplasty, post-pump syndrome in cardiopulmonary bypass or renal bypass, hemodialysis and renal ischemia.

18. A method for treating a lung disease or lung disorder involving complement comprising administering to a subject suffering from said lung disease or lung disorder, via the pulmonary route, a soluble complement receptor 1 (sCR1) polypeptide or fragment, derivative, or analog thereof in an amount effective to inhibit complement activity, wherein said sCR1 polypeptide or fragment, derivative or analog thereof retains at least one complement-binding activity of an erythrocyte CR1 allotype.

19. The method according to claim 18 in which the administered sCR1 is the same as that expressed by the Chinese Hamster Ovary cell DUX B11 carrying plasmid pBSCR1c/pTCSgpt as deposited with the ATCC and assigned accession number CRL 10052.

20. The method according to claim 18 in which the lung disease or lung disorder involving complement is selected from the group consisting of dyspnea, hemoptysis, asthma, chronic obstructive pulmonary disease (COPD), emphysema, pulmonary embolisms, and pulmonary infarcts.

21. The method according to claim 18 in which the lung disease or lung disorder involving complement is selected from the group consisting of pneumonia, fibrinogenic dust diseases, pulmonary fibrosis, organic dust diseases, exposure to irritant gasses and chemicals, hypersensitivity pneumonia, parasitic disease, Goodpasture's Syndrome, adult respiratory distress syndrome (ARDS) and pulmonary vasculitis.

22. The method acccording to claim 21 in which the fibrinogenic dust disease results from exposure to dust or minerals selected from the group consisting of silicon, coal dust, beryllium, and asbestos.

23. The method according to claim 21 in which the exposure to irritant gasses or chemicals is exposure to a gas or chemical selected from the group consisting of chlorine, phosgene, sulfur dioxide, hydrogen sulfide, nitrogen dioxide, ammonia and hydrochloric acid.

24. The method according to claim 18 in which the lung disease or lung disorder involving complement is bronchoconstriction.

25. The method according to claim 18 in which the lung disease or lung disorder involving complement results from a thermal injury to the lung.

26. The method according to claim 18 in which the lung disease or lung disorder involving complement results from a smoke inhalation injury to the lung.

27. A method for treating bronchoconstriction comprising administering to a subject suffering bronchoconstriction, via the pulmonary route, an aerosol formulation consisting essentially of a soluble complement receptor 1 (sCR1) polypeptide or fragment, derivative, or analog thereof and a pharmaceutically acceptable dispersant in an amount effective to inhibit complement activity, wherein said sCR1 polypeptide or fragment, derivative or analog thereof retains at least one complement-binding activity of an erythrocyte CR1 allotype.

28. The method according to claim 27 in which the administered sCR1 is the same as that expressed by the Chinese Hamster Ovary cell DUX B11 carrying plasmid pBSCR1c/pTCSgpt as deposited with the ATCC and assigned accession number CRL 10052.

29. The method according to claim 27 in which the bronchoconstriction results from smoke inhalation.

30. A method for treating anaphylaxis, idiopathic anaphylaxis, or an anaphylactoid reaction comprising administering to a subject experiencing anaphylaxis or an anaphylactoid reaction, via the pulmonary route, an aerosol formulation consisting essentially of a soluble complement receptor 1 (sCR1) polypeptide or fragment, derivative, or analog thereof and a pharmaceutically acceptable dispersant in an amount effective to inhibit complement activity, wherein said sCR1 polypeptide or fragment, derivative or analog thereof retains at least one complement-binding activity of an erythrocyte CR1 allotype.

31. The method according to claim 30 in which the administered sCR1 is the same as that expressed by the Chinese Hamster Ovary cell DUX B11 carrying plasmid pBSCR1c/pTCSgpt as deposited with the ATCC and assigned accession number CRL 10052.

* * * * *